(12) United States Patent
Springer et al.

(10) Patent No.: US 11,728,038 B2
(45) Date of Patent: Aug. 15, 2023

(54) ACTIVITY MRI

(71) Applicants: Oregon Health & Science University, Portland, OR (US); University of Washington, Seattle, WA (US)

(72) Inventors: Charles Springer, Portland, OR (US); Gregory Wilson, Seattle, WA (US); Jeffrey Maki, Seattle, WA (US); Thomas Barbara, Portland, OR (US); Xin Li, Portland, OR (US); William Rooney, Portland, OR (US); Wei Huang, Portland, OR (US); Brendan Moloney, Portland, OR (US); Eric Baker, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 456 days.

(21) Appl. No.: 16/497,513

(22) PCT Filed: Apr. 6, 2018

(86) PCT No.: PCT/US2018/026591
§ 371 (c)(1),
(2) Date: Sep. 25, 2019

(87) PCT Pub. No.: WO2018/187768
PCT Pub. Date: Oct. 11, 2018

(65) Prior Publication Data
US 2021/0304899 A1    Sep. 30, 2021

Related U.S. Application Data

(60) Provisional application No. 62/482,520, filed on Apr. 6, 2017.

(51) Int. Cl.
| | | |
|---|---|---|
| *G16H 50/50* | (2018.01) | |
| *G16H 30/20* | (2018.01) | |
| *G01R 33/563* | (2006.01) | |

(52) U.S. Cl.
CPC ....... *G16H 50/50* (2018.01); *G01R 33/56341* (2013.01); *G16H 30/20* (2018.01)

(58) Field of Classification Search
None
See application file for complete search history.

(56) References Cited

U.S. PATENT DOCUMENTS

| | | | |
|---|---|---|---|
| 6,751,495 B2 * | 6/2004 | Maier | G01R 33/56 324/307 |
| 2005/0007100 A1 * | 1/2005 | Basser | G01R 33/56341 324/300 |

(Continued)

OTHER PUBLICATIONS

White, Nathan S., and Anders M. Dale. "Distinct effects of nuclear volume fraction and cell diameter on high b-value diffusion MRI contrast in tumors." Magnetic resonance in medicine 72.5 (2014): 1435-1443.*

(Continued)

*Primary Examiner* — Sultana M Zalalee
(74) *Attorney, Agent, or Firm* — Schwabe, Williamson & Wyatt, P.C.

(57) ABSTRACT

Methods, computer-readable storage media and systems are described for constructing a three-dimensional electronic library of simulated decays of the diffusion-weighted $^1H_2O$ MR signal in b-space. Methods, computer-readable media, and systems are described for preparing a parametric tissue map for tissue in a subject. Computer readable media, having an electronic library of simulated decays of the diffusion-weighted $^1H_2O$ signal in b-space and method of using such a library.

27 Claims, 9 Drawing Sheets

(56) References Cited

U.S. PATENT DOCUMENTS

| | | | | |
|---|---|---|---|---|
| 2011/0043206 | A1* | 2/2011 | Kimura | G01R 33/56341 324/309 |
| 2011/0206256 | A1* | 8/2011 | Ramanathan | G16Z 99/00 382/128 |
| 2012/0280686 | A1* | 11/2012 | White | G01R 33/48 324/309 |
| 2013/0090548 | A1* | 4/2013 | Hamilton | A61B 5/201 600/419 |
| 2013/0278257 | A1* | 10/2013 | Boada | G01R 33/56341 324/309 |
| 2013/0317341 | A1* | 11/2013 | Spies | A61B 5/055 600/410 |
| 2015/0115957 | A1* | 4/2015 | Topgaard | G01R 33/565 324/309 |
| 2015/0253410 | A1* | 9/2015 | Warfield | G01R 33/5602 324/309 |
| 2015/0272467 | A1* | 10/2015 | Warfield | G01R 33/54 382/131 |
| 2015/0301142 | A1 | 10/2015 | Griswold et al. | |
| 2015/0309137 | A1 | 10/2015 | Bydder et al. | |
| 2016/0018504 | A1* | 1/2016 | Magin | A61B 5/055 324/309 |
| 2017/0124294 | A1* | 5/2017 | Perez | G06F 17/18 |
| 2017/0146629 | A1* | 5/2017 | Le Bihan | A61B 5/055 |
| 2018/0031663 | A1* | 2/2018 | Borsook | A61B 5/055 |
| 2018/0045802 | A1* | 2/2018 | Le Bihan | A61B 5/489 |
| 2018/0306885 | A1* | 10/2018 | Huwer | G01R 33/5608 |
| 2019/0033410 | A1* | 1/2019 | Ennis | G06T 7/0012 |

OTHER PUBLICATIONS

Chai, Wen-Yen, et al. "Magnetic-resonance imaging for kinetic analysis of permeability changes during focused ultrasound-induced blood-brain barrier opening and brain drug delivery." Journal of Controlled Release 192 (2014): 1-9.*

M. Nilsson et al., "Evaluating the Accuracy and Precision of a Two-Compartment Karger Model using Monte Carlo Simulations", Journal of Magnetic Resonance; 206 (2010) pp. 59-67.

C. Yeh, "Diffusion Microscopist Simulator—The Development and Application of a Monte Carlo Simulation System for Diffusion MRI", Universite Paris Sud—Paris XI: National Yang-Ming University (Taiwan), (2011), pp. 1-160.

G. T. Balls et al., "A Simulation Environment for Diffusion Weighted MR Experiments in Complex Media", Magnetic Resonance in Medicine; 62; (2009) pp. 771-778.

Mulkern et al., "On High B Diffusion Imaging in the Human Brain: Ruminations and Experimental Insights", In: Magn Reson Imaging, Oct. 2009; 27(8): 1151-1162.

Osuga et al., "Magnetic-Field Transfer of Water Molecules", In: Jornal of Applied Physics 106, 094311, 2009.

T. Imae et al., "Estimation of cell membrane permeability of the rat brain using diffusion magnetic resonance imaging", Journal of Applied Physics, American Institute of Physics, US, vol. 103, No. 7 Feb. 29, 2008, pp. 07A311-1-07A311-3.

T. Imae et al., "Estimation of cell membrane permeability and intracellular diffusion coefficient of human gray matter". Magnetic Resonance in Medical Sciences, vol. 8, No. 1, Apr. 1, 2009 pp. 1-7.

J. Clayden et al. "Microstructural parameter estimation in vivo using diffusion MRI and structured prior information", Magnetic Resonance in Medicine, vol. 75, No. 4, May 20, 2015, pp. 1787-1796.

* cited by examiner

ACTIVITY MRI

CROSS REFERENCE TO RELATED APPLICATIONS

The present application is a national phase entry under 35 U.S.C. § 371 of International Application No. PCT/US2018/026591 filed Apr. 6, 2016, entitled "ACTIVITY MRI," which designated, among the various States, the United States of America, and which claims priority to U.S. Provisional Patent Application No. 62/482,520 filed Apr. 6, 2017, which is hereby incorporated by reference.

ACKNOWLEDGEMENT OF GOVERNMENT SUPPORT

This invention was made with government support under Grant Numbers UO1-CA154602, and R44-CA180425 awarded by the National Institutes of Health. The United States government has certain rights in this invention.

FIELD

Generally, the field involves Magnetic Resonance Imaging (MRI), and more specifically, methods for simulation, monitoring, predicting and providing information about the translocation properties of water molecules in tissue.

BACKGROUND

Metabolic aspects lie at the heart of biology. Principal among these are the rates of enzyme-catalyzed biochemical reactions, called fluxes. It is not easy, or common, to measure such dynamic processes in living organisms. Moreover, modern gene expression array analyses suggest that, in most (if not all) tissues, metabolic fluxes are heterogeneous: i.e., their speeds differ in different tissue regions. This is surely crucial in all pathologies. For example, many researchers think a number of different cancer cell populations are present within a malignant tumor, and in metabolic competition for necessary nutrients. A therapy that kills only one cell type may liberate others to flourish.

Metabolic heterogeneity puts a premium on in vivo imaging with the highest possible spatial resolution. There are only a handful of human imaging modalities that can map metabolic fluxes, and these are found in the nuclear medicine (e.g., positron emission tomography (PET)) and magnetic resonance spectroscopic imaging (MRSI) fields. Unfortunately, their voxel sizes (tens of μL-few mL) are too large to discern most pertinent heterogeneity. Computed tomography (CT) and water proton ($^1H_2O$) MR imaging can easily provide images with 1 μL (or smaller) voxels anywhere in the human body. However, these have been thought restricted to mapping anatomical and vascular features.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings

DETAILED DESCRIPTION

Figure 1:
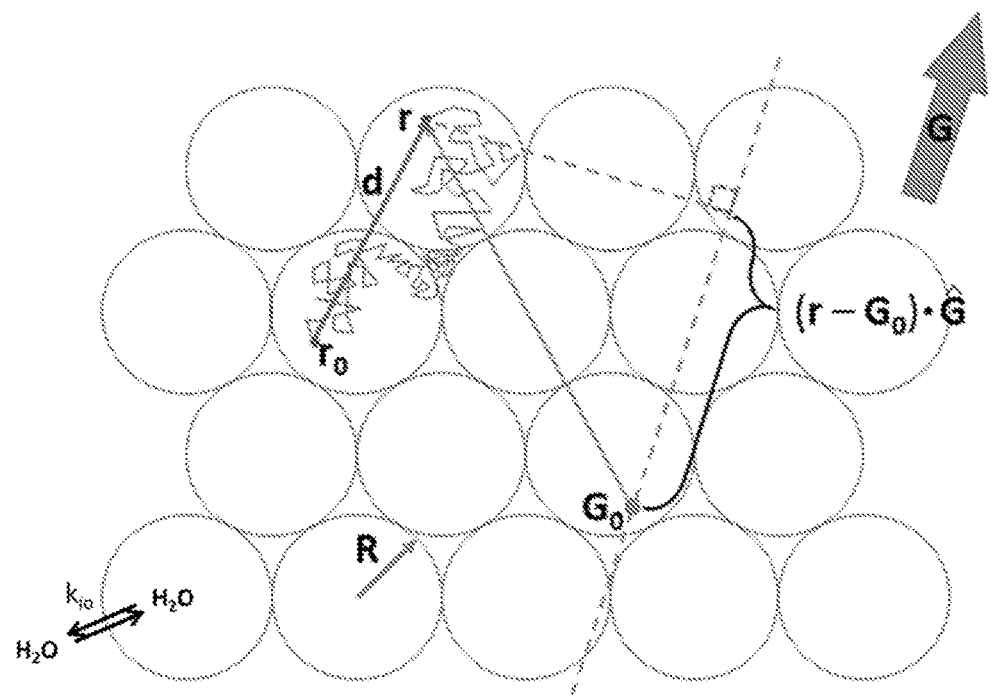
FIG. 1 shows a 2D cartoon of a random walk of a water molecule through a cellular ensemble.

In the following detailed description, reference is made to the accompanying drawings, which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Diffusion-weighted Magnetic Resonance Imaging (D-w MRI) is a major sub-field of clinical MRI. Among many applications in all body tissues, it is crucial in neurological scans for: acute stroke evaluation (lima M, and Le Bihan D, Radiology (2016) 278:13-32); circuit tracing in resting-state functional connectivity (Glasser M F et al., Nat. Neurosci. (2016) 19: 1175-1187); and brain cancer therapy evaluation (Hamstra D A et al., Proc. Nat. Acad. Sci. (2005) 102:16759-16764). There has even been an exploration of functional MRI (cerebral activity) based on brain water diffusion (Le Bihan D, et al., Proc. Nat. Acad. Sci. (2006) 103:8263-8268). However, this wide-spread use is of a rather empirical nature. There has never been a satisfactory biophysical explanation for the absolute nature of D-w MRI signals (lima M, and Le Bihan D, Radiology (2016) 278:13-32; Nevo U, et al., NMR Biomed. (2010) 23:734-744).

The essence of the elegant D-weighting experiment is to encode information into the MRI signal about how far tissue water molecules can move during a period of time fixed by the experimenter—so-called water "diffusion." This method was initiated for inanimate samples more than 50 years ago (Stejskal E O, et al., J. Chem. Phys. (1965) 42:288-292). It employs the imposition of prescribed transient magnetic field spatial gradients and radio frequency pulses to "echo" stimulated NMR signals. A prescribed magnetic field gradient (MFG) is a controlled change of magnetic field strength in a given distance. The amount of the signal lost at the echo is proportional to the distance spin-bearing molecules moved during the period between pulses. It works perfectly well to determine the diffusion coefficient (D) values for solvent and solute molecules in homogeneous fluid samples. For these, the concept of the normalized b parameter (the product of the diffusion time and the square of the gradient effectiveness) was introduced. For homogeneous samples, the decay of D-w NMR signals in "b-space" is well-described as a single exponential function. A plot of the logarithm of the fractional decay (S/S$_0$) vs. b yields a straight line with slope equal to −D. The use of b corrects for almost all possible experimental differences from different instruments at different institutions. It is essentially absolute.

However, biological tissue is not homogeneous. More than 99% of all human MR images are made from the water proton NMR signal, $^1H_2O$. And, one of the essences of tissue is that water molecules are compartmentalized: the major distinction is between intra- and extracellular water. Millions of years of evolution have produced cell membranes that are relatively impermeable to water, and almost all solute molecules. This has allowed development of membrane enzymes that provide cellular control of solute molecule transport into and out of the cell.

It has long been recognized that cell membranes present a "hindrance," or "restriction," to water translation in tissue. A major manifestation of this is that the decay of the tissue D-w $^1H_2O$ signal in b-space is clearly not mono-exponential. Thus, the concept of D no longer has meaning in this situation. Thus, the clinical applications indicated above have proceeded using only relative changes of the decay shape.

It has also been discovered that the permeability of the cell membrane to water has a contribution that is under active cellular metabolic control. The rate constant for equilibrium cellular water efflux, $k_{io}$, is proportional to the activity of the cell membrane $Na^+,K^+$-ATPase (NKA) (Zhang Y, et al., Biophys. J. (2011) 101:2833-2842; Springer C S, Li X, et al., NMR Biomed. (2014) 27:760-773).

Furthermore, the on-going activity of NKA, one of biology's most crucial enzymes, is not currently measurable in an intact organism. The operation of NKA is responsible for maintaining the vital $Na^+$ and $K^+$ trans-membrane concentration gradients, and the electrical potential across the cell membrane. That these are crucial features of a cell's vitality is shown by the fact that, in almost all cases, much more than half of the temporal production of the cell's most important energy molecule, adenosine triphosphate (ATP), is used to support the NKA pump's continual operation. In recent work, the inventors found that numerical computer simulations of random water molecule displacement in tissue, including provision for $k_{io}$, and the intracellular volume fraction, $v_i$, proved remarkable in describing the absolute transverse $^1H_2O$ relaxation in blood without any adjustable parameters (Wilson G J et al., *Magn. Reson. Med.* (2017), incorporated by reference herein).

As disclosed herein, the inventors applied simulations to the D-w MRI problem, see Examples 1, 2, and 3. FIG. 1 shows a 2D cartoon of a random walk of a water molecule through an ensemble of cells. The molecule started at position $r_0$, and eventually translocated or "walked" to position r in a 80 ms time period. The random steps occur both inside a spherical cell and outside in the spaces between the spherical cells. The hindrance to displacement is obvious in both spaces. The direction of a magnetic field gradient (MFG) of strength G, and centered at Go, is also indicated. In practice, the simulations are carried out in 3D with the cartoon represented in 2D for simplification. Though each "walk" is random by itself, a multiplicity, such as thousands, of random walks can be computed, and the average characterized.

The Einstein equation predicts that, for a homogeneous medium, the mean of the squares of the displacement distances, $\langle d^2 \rangle$, will increase linearly with the time "walked," and the slope is equal to 6D (the result of a single Gaussian process). If $k_{io}=0$ (no permeability), such behavior is not observed for either intra- or extracellular water molecules (see Example 1, FIG. 2). As described in Example 1, simulations were carried out for reasonably pertinent tissue properties; an intracellular water volume fraction ($v_i$)=0.74, and cell radius (R)=15 μm. When the permeability values were incremented up to $k_{io}=100$ $s^{-1}$, the $\langle d^2 \rangle$ vs. time plots remain hyperbolic (see Example 1 and FIG. 3). Since the instantaneous tangents (6D) continually decrease, there are infinite numbers of D values [an infinite number of Gaussians], and the concept of an overall D value for tissue water does not apply. Only when the permeability is made infinite ($k_{io}=\infty$) is there a linear plot with a defined D (see Example 1 and FIG. 3). It is important to note that the $\langle d^2 \rangle$ achieved at a given diffusion time depends strongly on $k_{io}$: the larger $k_{io}$, the larger $\langle d^2 \rangle$ (see Example 1, FIG. 3).

Considering only the translocation of water molecules in tissue, in order to encode displacement information into the $^1H_2O$ MR signal, a magnetic field gradient (MFG) is imposed. The vector for one, of strength G and centered at Go, is shown in FIG. 1. In Example 2 simulated log $(S/S_0)$ decays in b-space were performed for various $k_{io}$ values (with $v_i$=0.74 and R=15 μm) (See FIGS. 4 and 5). The decays were very sensitive to the value of $k_{io}$. Once again, it is important to note that such a plot is linear for only infinite permeability ($k_{io}=\infty$), in which case the slope is –D, as if the ensemble is homogeneous (no cell membranes, or no cells): a single exponential function. The concept of D is not defined for any finite permeability. As $k_{io}$ goes from 100 $s^{-1}$ to 30 $s^{-1}$ to 10 $s^{-1}$ to 2 $s^{-1}$ to 0 $s^{-1}$, the increasing upward curvature becomes very obvious. In each of these cases, there are an infinite number of exponential functions; i.e., an infinite number of D (negative instantaneous tangent) values.

Figure 4:
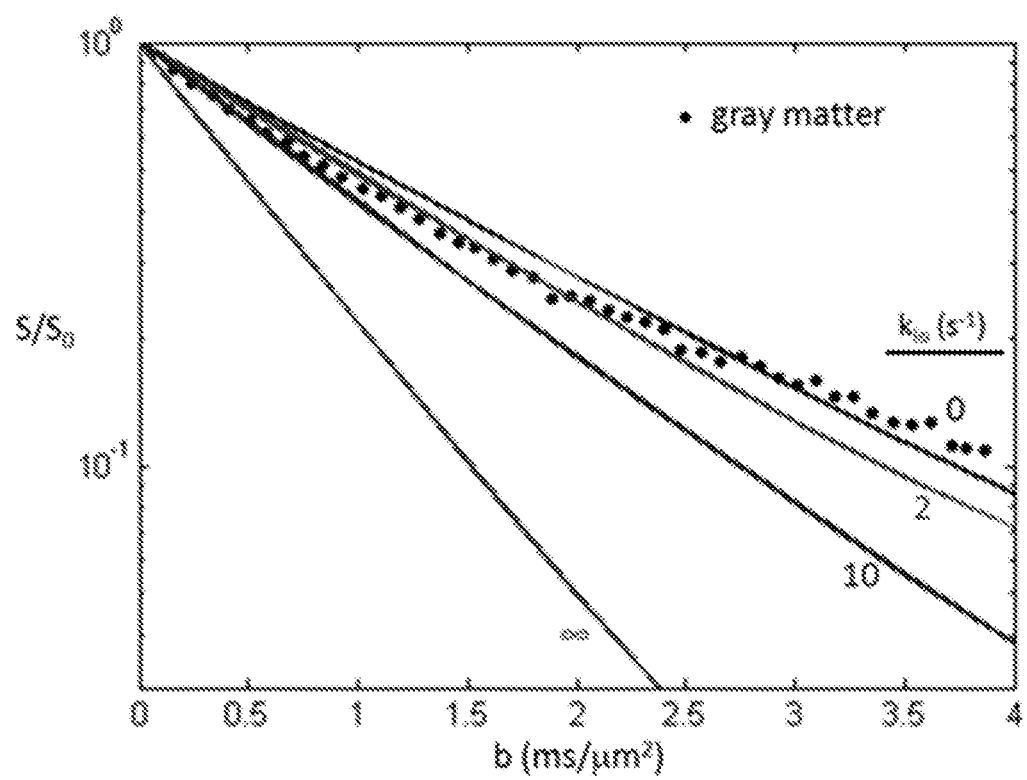
FIG. 4 shows semilog plots of simulated D-w $^1H_2O$ signals vs. b ($v_i$=0.74, R=15 μm, and $k_{io}$=0, 2, 10 s$^{-1}$, and ∞). Only the $k_{io}$=∞ curve is linear in this semilog plot, as expected for "free" diffusion. The $k_{io}$=0, 2, and 10 s$^{-1}$ plots curve upward. The parameter b is a normalized measure of MR coherence de-phasing. Experimental data (marked with dots in the figure) were acquired at 1.5 T from a 3.3 mL region-of-interest (ROI) in human cortical gray matter.
Figure 5:
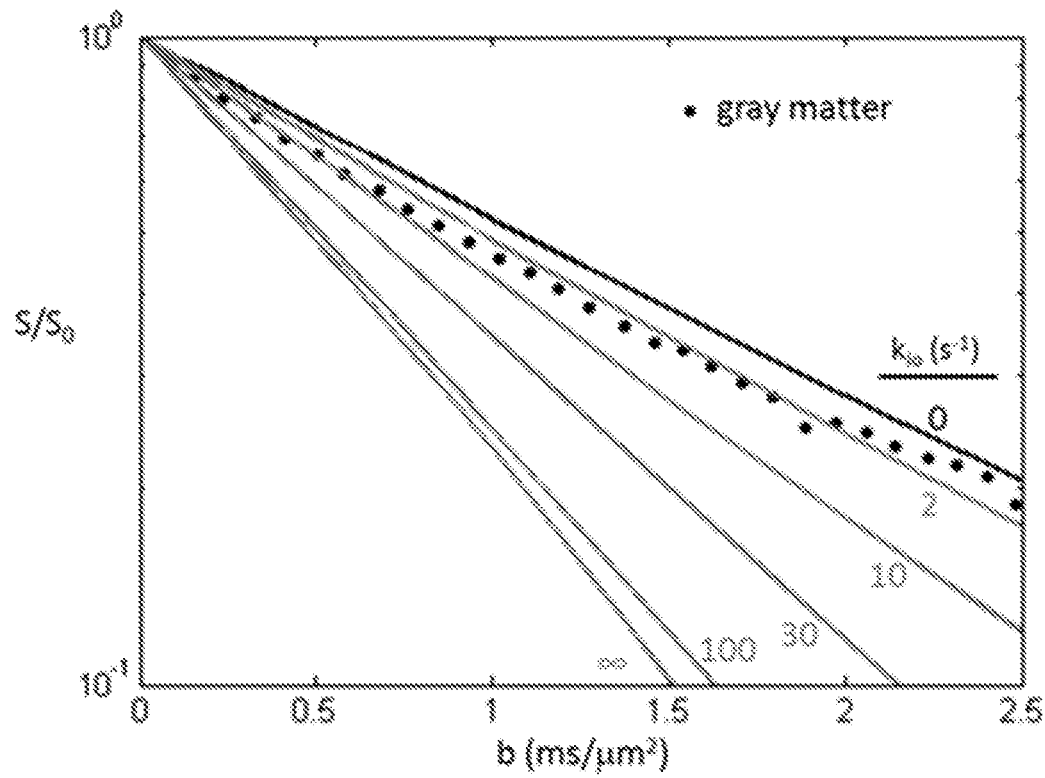
FIG. 5 shows semilog plots of simulated D-w $^1H_2O$ signals vs. b ($v_i$=0.74, R=15 μm, and $k_{io}$=0, 2, 10, 30, 100 s$^{-1}$, and ∞). This figure expands the early portion (to b=2.5 ms/μm$^2$) of FIG. 4, illustrating the strong dependence of the initial slope on $k_{io}$.

Turning to the $k_{io}=2$ $s^{-1}$ decay curves in FIGS. 4 and 5, comparisons are made to experimentally obtained data. For anesthetized rat brain (mostly gray matter-like), $k_{io}$ is 1.8 $s^{-1}$ and, for brain gray matter in general, $v_i$ is 0.8. For comparison, high quality experimental points were plotted for a 3.3 mL cortical region-of-interest in human cerebral gray matter (denoted as filled circles in the plots of FIGS. 4 and 5) taken from the literature. The agreement between the simulated decay curves and the plotted experimental points is apparent, even in the absence of any formal "fitting" procedure. The systematic nature of the residuals (negative for b<2, positive for b>2) suggests the data could be well-fitted by a simulation having relatively small adjustments of intracellular water volume fraction $v_i$ and/or cell radius R. Of note, the b-space decay is different for cerebral white matter. The differences in b-space decay for different tissue types allows the b-space decay values to be used to map tissue types in an experimental MRI analysis, for example at the voxel level, to create parametric maps.

The initial slopes of the b-space decays are emphasized in FIG. 5. These initial slopes are seen to be quite sensitive to the $k_{io}$ value. This, and the agreement with the experimental data, suggests that the initial slope may be dominated by the $k_{io}$ parameter. The later experimental data curvature can likely be fitted by adjustment of the $v_i$ and/or R parameters in the computer simulations. Thus, a realistic biophysical molecular description of the D-w $^1H_2O$ signal is achievable using the proposed models.

The negative asymptotic slope of the b-space decay is referred to as the Apparent Diffusion Coefficient (ADC). Despite the fact that it is difficult to measure experimentally, it is still used clinically as an imaging biomarker. Almost all of the clinical applications of D-w MRI employ relative changes of ADC in some fashion.

The simulation technique described herein can also be cast in terms of the cell number density, ρ, and average cell volume, V, rather than intracellular water volume fraction, $v_i$, and cell radius, R, to model a parenchymal tissue cell ensemble (the parameter $k_{io}$ is retained in this embodiment). The $v_i$ quantity is equal to the cell number density times the cell volume (ρ·V), and cell radius R is proportional to $V^{1/3}$. The parameters $k_{io}$, ρ, and V represent fundamental tissue properties and are vital tissue biomarkers. As mentioned above, $k_{io}$ measures the cell's metabolic rate of NKA ($MR_{NKA}$), ρ is a quantitative measure of "cellularity" (usually approximated only qualitatively), and V is a measure of edema—reflected in cell swelling or shrinking. Since even a high-resolution $^1H_2O$ MRI voxel contains hundreds of thousands of different cells, it is to be understood that $k_{io}$, ρ, and V values in high-resolution parametric maps will represent the voxel-averaged values; $\langle k_{io} \rangle$, $\langle \rho \rangle$, and $\langle V \rangle$. Further, it is to be understood that this model is avascular, and has no inherent anisotropy, but is intended for generalized parenchyma. Since it has never been possible to measure these fundamental properties in vivo, this presents an important contribution to the interpretation and application of D-w MRI.

Figure 7A:
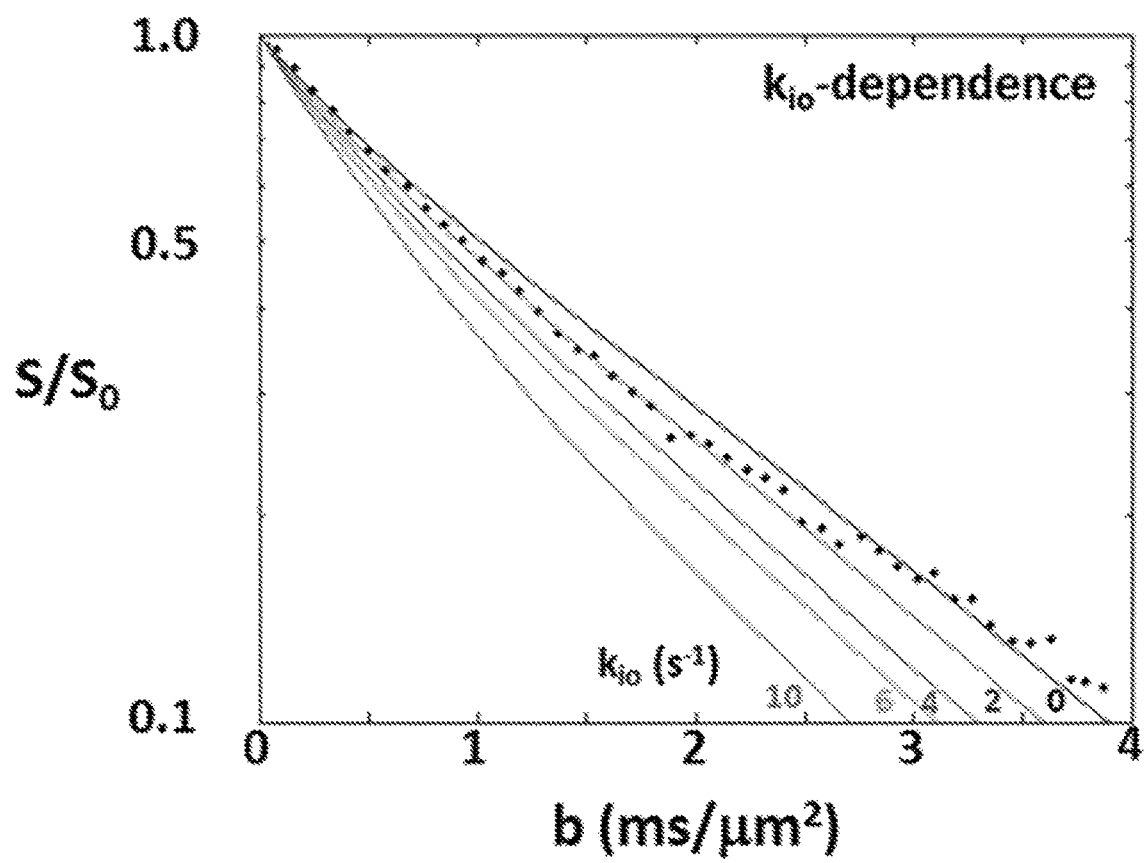
FIG. 7A shows semilog plots of simulated D-w $^1H_2O$ signals vs. b from Monte Carlo random walk simulated D-w MRI decays. The ordinate measures log (S/S0), where S is the transverse $^1H_2O$ MR signal, and S0 is its maximum value. The abscissa measures the normalized coherence de-phasing b value. In this plot, the parameters V (mean cell volume) and ρ (cell density) were held fixed at 9.2 pL and 80,400 cells/μL, respectively. Decays for five $k_{io}$ values: 0, 2.0, 4.0, 6.0, and 10.0 s$^{-1}$ are shown. Experimental data from a 3.3 mL human cerebral cortex ROI are shown as diamonds.
Figure 7B:
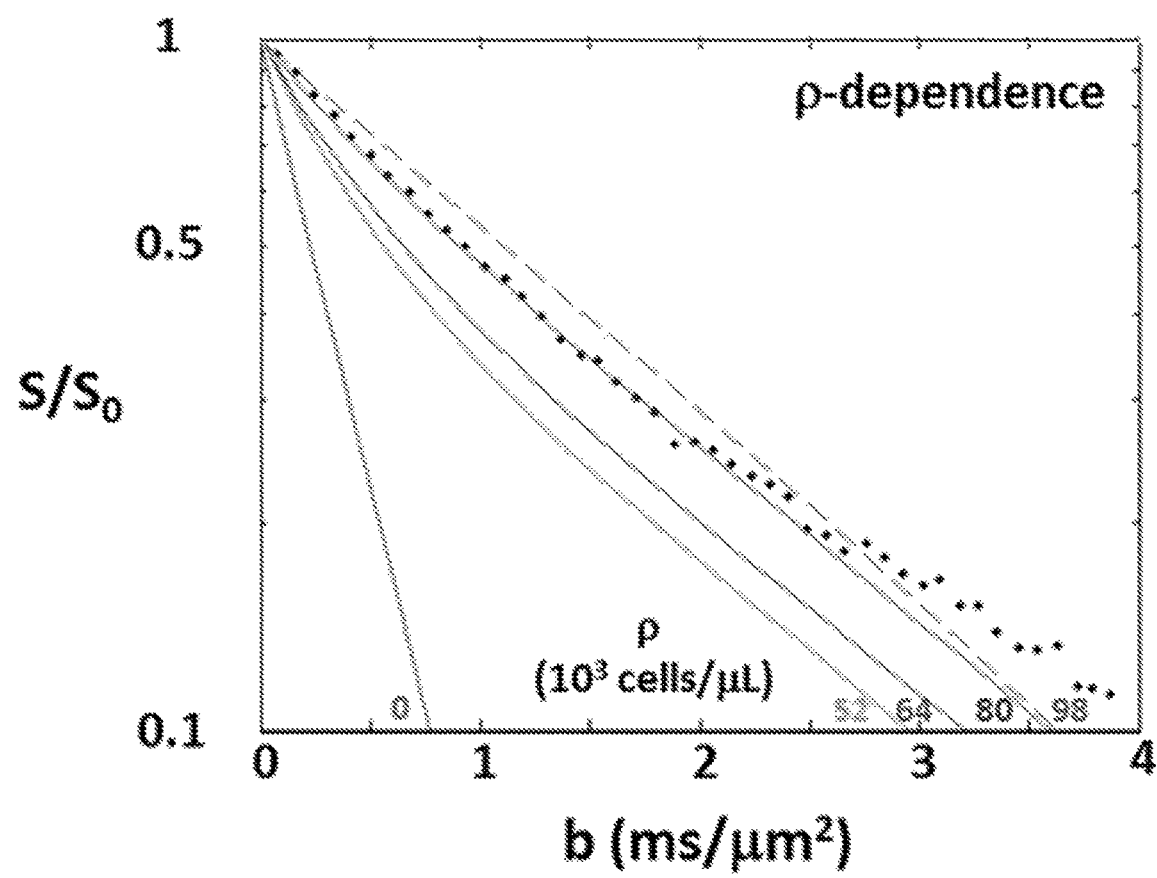
FIG. 7B shows semilog plots of simulated D-w $^1H_2O$ signals vs. b from Monte Carlo random walk simulated D-w MRI decays. The ordinate measures log (S/S0), where S is the transverse $^1H_2O$ MR signal, and S0 is its maximum value. The abscissa measures the normalized coherence de-phasing b value. In this plot, V and $k_{io}$ were fixed at 9.2 pL and 2.0 s$^{-1}$, respectively. Decays for five ρ values: 0; 52,400; 64,400; 80,400; and 97,800 cells/μL are shown. Experimental data from a 3.3 mL human cerebral cortex ROI are shown as diamonds.
Figure 7C:
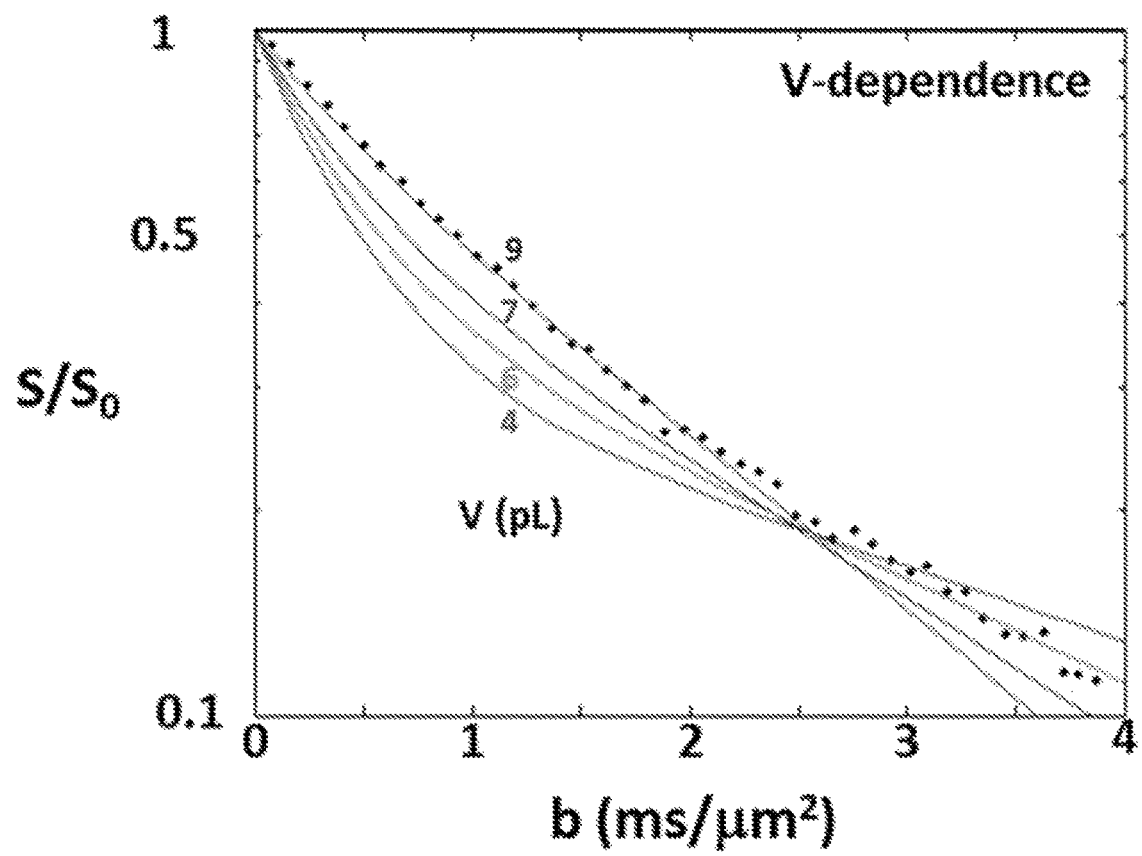
FIG. 7C shows semilog plots of simulated D-w $^1H_2O$ signals vs. b from Monte Carlo random walk simulated D-w MRI decays. The ordinate measures log (S/S0), where S is the transverse $^1H_2O$ MR signal, and S0 is its maximum value. The abscissa measures the normalized coherence de-phasing b value. In this plot, the parameters ρ and $k_{io}$ were fixed at 80,400 cells/μL and 2.0 s$^{-1}$, respectively. Decays for four V values: 4.2, 5.6, 7.2, and 9.2 pL are shown. Experimental data from a 3.3 mL human cerebral cortex ROI are shown as black diamonds.

FIGS. 7A, 7B, and 7C present families of simulations varying each of these parameters ($k_{io}$, ρ, and V, respectively) in turn. The plots result from an exemplary simulation of Monte Carlo random walks in an ensemble of 10,648 monodisperse spheres having hexagonal close-packed symmetry. The unrestricted diffusion coefficient at 37° C., $D_0$=3.0 μm²/ms, was used for all particles, whether inside or outside cells. The panels have ordinates that measure log[S(b)/S$_0$], where S(b) is the D-w signal intensity and S$_0$ the total transverse signal intensity immediately after coherence creation, and abscissae that report the normalized coherence decay measure, b. The quantity b≡$(\gamma G\delta)^2 t_D$: where $\gamma$ is the $^1$H magnetogyric ratio, G is the PFG strength, $\delta$ the PFG duration, and the diffusion time $t_D$≡$[\Delta-(\delta/3)]$, where $\Delta$ is the interval between the PFG pair leading edges (see lima M, and Le Bihan D, Radiology (2016) 278:13-32). The b factor accounts for de-phasing during the PFGs [the $(\gamma G\delta)^2$ factor] and de-phasing by diffusion during $\Delta$ [the $t_D$ factor]. Note that the unit of b used here, ms/(μm)$^2$, is 10$^3$ that of s/(mm)$^2$ commonly used in the literature; i.e., b values with the latter unit are 10$^3$ larger.

For FIG. 7A decays, V was held fixed at 9.2 pL (cell radius, R=13 μm) and $\rho$ at 80,400 cells/μL ($\rho$=$v_i$/V: the intracellular volume fraction, $v_i$=1-$v_e$; here, $v_i$=0.74, the cells were touching). Decays for five $k_{io}$ values, 0, 2.0, 4.0, 6.0, and 10.0 s$^{-1}$, are shown. The $k_{io}$-dependence is demonstrated. The decays are non-linear in these semi-log plots indicating non-Gaussian behavior. The decays are relatively sensitive to $k_{io}$: the larger $k_{io}$ the steeper the decay. This is sensible: on the average, water molecules can move further, and de-phase more, the more permeable the cell membranes. Since the apparent diffusion coefficient [ADC] is an empirical measure of the negative of the asymptotic {ln(S(b)/S$_0$)/b} slope, the ADC increases with $k_{io}$, for constant q and V (see description below of FIG. 8A).

For FIG. 7B decays, V was held fixed at 9.2 pL and $k_{io}$ at 2.0 s$^{-1}$. Decays for five $\rho$ values, 0, 52,400, 64,400, 80,400, and 97,800 cells/μL, are shown. The $\rho$-dependence is displayed. For the case where $\rho$=97,800 cells/μL, the spherical cells had to be deformed slightly toward cubes. The $v_i$ of 0.90 (97.8×10$^3$ cells/μL) could not be reached with close-packed spheres. Also, the symmetry of the ensemble was slightly altered. The decay for zero cells/μL, pure water, is linear, indicating a Gaussian diffusion process with ADC=D$_0$=3.0 μm$^2$/ms. In this figure, the decays become less steep with increasing $\rho$: ADC decreases with increasing $\rho$. This is also sensible: water molecules cannot move as far, the greater the cellularity. The decay is sensitive to $\rho$, but note the range from 52,400 to 97,800 is 45,400 cells/μL, a very large cell density increase.

For FIG. 7C decays, $\rho$ was held fixed at 80,400 cells/μL and $k_{io}$ at 2.0 s$^{-1}$. Decays for four V values, 4.2, 5.6, 7.2, and 9.2 pL, are shown. The V-dependence is demonstrated in this figure, which is more complicated than in FIGS. 7A and 7B. At small b values, cell swelling causes less steep decays (i.e., decreasing ADC; the conventional wisdom) but at larger b values it causes increased steepness. Note the range from 4.2 to 9.2 pL is a more than doubling of the cell volume; a large increase. The decay curves in FIG. 7C also exhibit a curious "isosbestic" point near b=2.5 2.5 ms/(μm)$^2$. It is near this same b value that the $k_{io}$=2 s$^{-1}$ curve begins to dive below the experimental data in FIG. 7A. The inventors have discovered when simulations are carried out to much greater b values (for example, greater than b=10 ms/(μm)$^2$), the decay curves exhibit non-monotonic "dips" at very small log(S/S0) values [not shown], which are below most experimental noise levels. Thus, the curves must have inflection points: the isosbestic point may be such a point as well. Experimental data out to high b values do not exhibit such abnormalities. Therefore, these are most likely Bragg "diffraction" effects, expected because of the monodispersity and/or periodicity of the digital ensemble to conduct the present simulations. In embodiments, the use of polydisperse "Voronoi" cells or other non-uniform and/or non-periodic domains for the spherical or cuboid cells can be used in simulations to eliminate this effect. Thus, it is contemplated that simulations to generate electronic library (dictionary) entries of b-space decays are not limited to the use of ensembles of spherical of close-packed cell domains for computation, but may also comprise polydisperse cell arrangements having non-uniform and non-periodic size and spacing.

FIGS. 7A, 7B, and 7C also show in vivo experimental data (plotted with diamond markers) plotted alongside the families of decay curves. These in vivo data were obtained from a 3.3 mL ROI in human cerebral cortex. These data are well known in the literature, and have been shown to perfectly match other data from rat brain for a 63 μL ROI and a 125 μL ROI. This comparison confirms the robustness of the b normalization. The results were obtained at different institutions, different field strengths, with different acquisition strategies [(b-incrementation)$_{tD}$ vs. (b-incrementation)$_G$], and out to varied b values.

It is also noteworthy that one simulation presented in FIGS. 7A-7C matches the experimental data remarkably well, especially at lower b values, out to about 2.5 ms/(μm)$^2$ (i.e., 25,000 s/(cm)$^2$). This is the curve corresponding to the parameter values $k_{io}$=2.0 s$^{-1}$, $\rho$=80,400 cells/μL, and V=9.2 pL in each of FIGS. 7A-7C.

As noted above, it has not before been possible to measure $k_{io}$, $\rho$, or V in vivo. This is particularly consequential for the mean cell volume V. For example, if one employs ex vivo fixed tissue histology, one finds the specimen intra- and extracellular space water distribution is strongly affected by the fixing solution osmolality, a fact often overlooked. Obviously, this would affect the micrographic estimation of cell volumes. However, careful optical microscopy of living cells in culture does indeed yield small numbers of pL as typical for V distribution means or medians. Thus, the cell volume, V, parameter is also in excellent agreement with what is expected in vivo. Taken together, the results presented in FIGS. 7A-7C suggest that the major determinants of water diffusion in tissue are the "concentration" of membranes (inversely), and their permeability (directly). Thus the parameters $k_{io}$, $\rho$, and V are sufficient to characterize tissue for this purpose. No "viscosity" considerations are needed.

The results in FIGS. 7A, 7B, and 7C may shed light on a number of D-w MRI observations prevalent in the literature. Though the disclosed simulation of $k_{io}$ treats the parameter it as if it's completely passive (i.e., $k_{io}$(p)), it is known that $k_{io}$ values extracted from experimental data (such as the points overlaid in FIGS. 7A-7C) also include an active component (i.e., a $k_{io}$(a) term as shown in Example 3 below). Since $k_{io}$(a) reflects a fast metabolic rate ($^cMR_{NKA}$ may be 50 fmol(ATP)/s/cell), one might expect acute ADC changes to be dominated by $^cMR_{NKA}$ changes, which could be very fast. Often, fast ADC changes have been interpreted in the literature exclusively in terms of V changes. FIG. 7C indicates that ADC is indeed sensitive to V, but it is important to note that large V changes are required, and that these represent the V averaged over a very large number of cells, e.g., 80,400 cells in a voxel. Thus, one might expect sufficient V changes to be slower than $k_{io}$ changes.

Figure 8A:
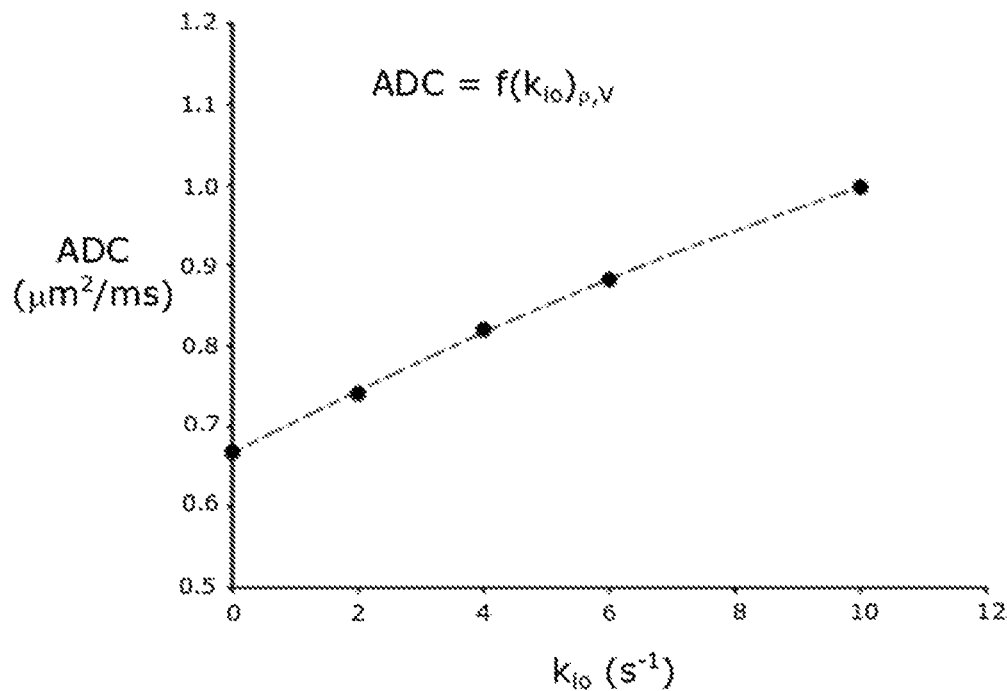
FIG. 8A shows a plot of the empirical apparent diffusion coefficients (ADCs) calculated from the simulated decays in FIG. 7A. These data were generated, per convention, by drawing a straight line between the ln(S/S0) values at b=0 and b=1 for each FIG. 7A curves. The ADC value is the negative of the slope of this line. The plot shows ADC=f$(k_{io})_{\rho,V}$, the $k_{io}$-dependence of ADC at constant $\rho$ and V.
Figure 8B:
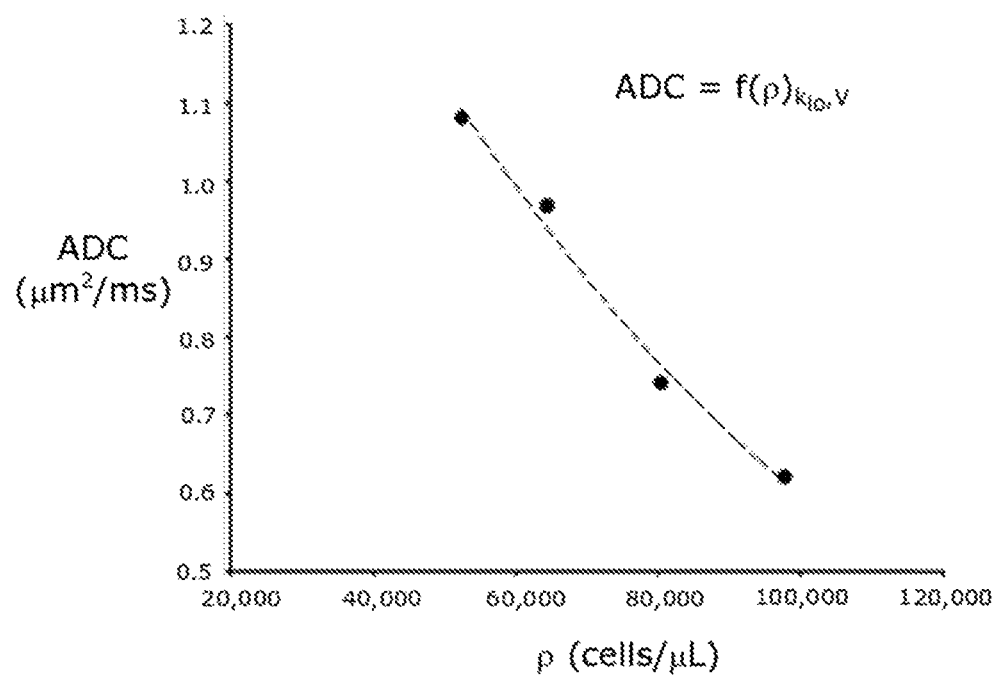
FIG. 8B shows a plot of the empirical apparent diffusion coefficients (ADCs) calculated from the simulated decays in FIG. 7B. These data were generated, per convention, by drawing a straight line between the ln(S/S0) values at b=0 and b=1 for each FIG. 7B curves. The ADC value is the negative of the slope of this line. The plot shows ADC=f$(\rho)_{kio,V}$, the $\rho$-dependence of ADC at constant $k_{io}$ and V
Figure 8C:
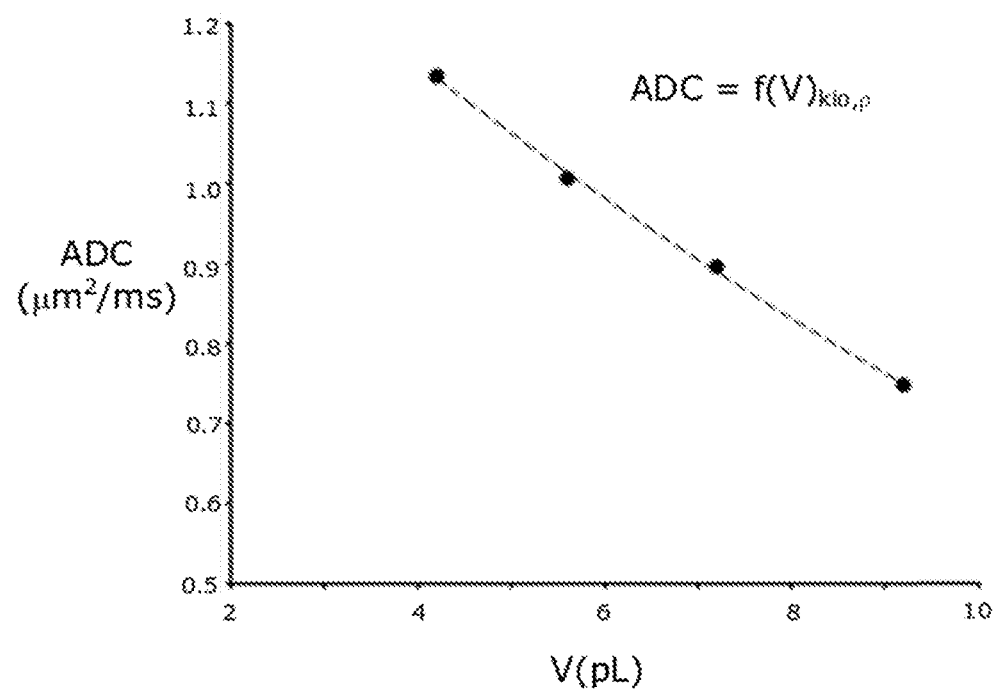
FIG. 8C shows a plot of the empirical apparent diffusion coefficients (ADCs) calculated from the simulated decays in FIG. 7C. These data were generated, per convention, by drawing a straight line between the ln(S/S0) values at b=0 and b=1 for each FIG. 7C curves. The ADC value is the negative of the slope of this line. The plot shows ADC=f(V)$k_{io,\rho}$, the V-dependence of ADC at constant $k_{io}$ and $\rho$.

An important aspect of the disclosed methods is the generation of formal fittings of experimental voxel b decays to produce $k_{io}$, $\rho$, and V parametric maps. However, the clinical implications of the disclosed method can also be appraised by estimating the empirical ADC values, so often reported in the literature and used in clinical applications, for the simulated decays of FIGS. 7A-7C. ADC values can be calculated using the straight lines between the ln(S/S$_0$) values at b=0 and b=1 for each of the plotted curves. The results are shown in FIGS. 8A, 8B, and 8C. In the process of an actual data fitting, the parameters will interact with each other during the iterations. Thus, to make clear the assumptions inherent in FIGS. 7A-7C, the ADC curves are labeled as follows: for FIG. 8A, where ADC is a function of $k_{io}$ and the values of ρ and V are held constant, the simulation results are notated ADC= $f(k_{io})_{ρ,V}$. Similarly, FIG. 8B is notated ADC=$f(ρ)_{kio,V}$, and FIG. 8C is notated ADC=shows ADC=$f(V)_{kio,ρ}$.

The findings disclosed herein allow for the construction of three-dimensional electronic library (also termed a "dictionary") of simulated decays of the diffusion-weighted $^1H_2O$ signal in b-space, which can be used to prepare parametric tissue maps of experimental and/or clinical D-w $^1H_2O$ MRI data and/or images. Disclosed herein in various embodiments are methods, computer-readable storage media and systems for constructing a three-dimensional electronic library of simulated decays of the diffusion-weighted $^1H_2O$ signal in b-space. Also disclosed are computer readable media, having an electronic library of simulated decays of the diffusion-weighted $^1H_2O$ signal in b-space and methods of using such a library, for example methods, computer-readable media, and systems for preparing a parametric tissue map for tissue in a subject.

Aspects of this disclosure relate to methods for constructing a three-dimensional electronic library of simulated decays of the diffusion-weighted $^1H_2O$ signal in b-space. In embodiments, these methods include constructing, with one or more computing devices, one or more models of water molecules in an ensemble of close-packed cells within a magnetic field. In some embodiment, the ensemble of cells can be modeled with a radius (R) and a rate constant for equilibrium cellular water efflux ($k_{io}$), and an intracellular volume fraction ($v_i$). In embodiments, the methods include simulating, with one or more computing devices, a set of random walks of the water molecules in the ensemble of close-packed cells, wherein the simulation comprises: applying a first magnetic field gradient prior to initiation of the random walks, the first magnetic field gradient sequence encoding positional information of a $^1H_2O$ spin precessional phase; initiating, the random walks of the water molecules for a period of time in the ensemble of close-packed cells; applying a second magnetic field gradient, the second magnetic field gradient sequence being the reverse of the first magnetic field gradient sequence; and determining the decay of the diffusion-weighted $^1H_2O$ signal. In embodiments, the results of the simulations are stored and thereby constructing the three-dimensional electronic library of simulated decays of the diffusion-weighted $^1H_2O$ signal in b-space. The stored three-dimensional electronic library of simulated decays of the diffusion-weighted $^1H_2O$ signal in b-space can be used immediately, or later, for example to prepare a parametric tissue map for tissue in a subject. In certain embodiments, the random walk proceeds for about 40 ms to about 120 ms, such as 80 ms, although shorter or longer time periods are envisioned. In embodiments, the close packed cells are modeled as generally spherical cells, although non-spherical cells are also envisioned, such as spherical cuboids or polygonal cells (such as Voronoi cells) among others. In addition, the ensemble of cells used for computational simulation may be non-uniformly spaced and non-uniformly sized. In embodiments, the average cell radius is about 3 μm to about 20 μm, such as 15 μm, although smaller or larger cell radii are envisioned. In embodiments, the cells have various radii in different simulations, for example to create an ensemble of simulations with cells of different radii approximating the different cell radii of cells in tissue. In embodiments, the intracellular volume fraction ($v_i$) is about 0.5 to about 1.0, such as about 0.74. In embodiments, the rate constant for equilibrium cellular water efflux ($k_{io}$) is varied in different simulations, for example to create an ensemble of simulations with different $k_{io}$ approximating the variation of $k_{io}$ in different cell types and/or tissue. In embodiments, the simulations and simulation results may be parameterized according to the rate constant for equilibrium cellular water efflux ($k_{io}$), the cell number density (ρ), and the mean cell volume (V). In embodiments, the simulations comprise Monte Carlo simulations, although other types of simulations can be used. Also disclosed is a computer readable media, comprising a non-transitory, computer-readable storage medium having computer-executable program instructions embodied therein for a method for constructing a three-dimensional electronic library of simulated decays of the diffusion-weighted $^1H_2O$ signal in b-space. The three-dimensional electronic library serves as a dictionary comprised of simulated decay curves, each decay curve indexed by the simulation parameters from which it was generated. For example, a given simulated decay curve in the dictionary can be associated with specific parameter values for $k_{io}$, ρ, and V (the rate constant for equilibrium cellular water efflux, the cell number density, and the mean cell volume, respectively).

Aspects of this disclosure concern methods of preparing a parametric tissue map for tissue, for example in a subject. The methods include: receiving D-w MRI acquisition data; determining the b-space decay of one or more, such as each, of the voxels in the D-w MRI acquisition data; and selecting a simulated decay of the diffusion-weighted $^1H_2O$ signal in b-space from an electronic library [or dictionary] of simulated decays of the diffusion-weighted $^1H_2O$ signal in b-space that matches the b-space decay of this voxel in the D-w MRI acquisition data, thereby preparing a parametric tissue map of the D-w MRI acquisition data. Also disclosed is a computer readable storage medium having computer-executable program instructions embodied therein for a method of preparing a parametric tissue map for tissue in a subject.

Aspects of the disclosure concern libraries and/or databases of simulated decays of the diffusion-weighted $^1H_2O$ signal in b-space, for example constructed using the methods described herein. Such data, such as the simulations and/or MRI image data can be stored in a machine-readable format for later use, such as in a database or library (also termed a dictionary). The present disclosure also provides for a machine-readable data storage medium, which comprises a data storage material encoded with machine readable data defining the simulated decays of the diffusion-weighted $^1H_2O$ signal in b-space, for example constructed using the methods described herein. Machine readable data storage material can be used to compare the experimental b-space decay of voxels in a high-resolution D-w MRI acquisition with every simulation systematically, for example systematically compared with every library entry to find the best match, and hence the correct parametric values to produce a tissue map. In embodiments, this matching is done with an efficient matrix algebra approach. For example similarity may be judged by algebraic and statistical methods well known in the art and embodied as standard features in available software pattern recognition packages. In other embodiments, this matching is performed using a "fingerprinting" approach (see for example, Christen T, et. al., Neuroimage. (2014), 89:262-70) to determine the best fit between experimentally observed b-space decays and numerical simulation library [or dictionary] entries. The result will be $k_{io}$, $v_i$, and V values for each pixel, or alternatively, $k_{io}$, $\rho$, and V values for each pixel, and thus a parametric tissue map for the MRI image or set of images may be generated. In particular, parametric mapping of the $k_{io}$ parameter provides a contrast agent-free method of in vivo of metabolic imaging as disclosed herein. Assembly/generation and consultation of such libraries may be automated using a computer executable software program. Libraries can be accessed through a user interface. Examples of such a user interface include, without limitation, electronic devices, such as a computer or a hand held device. The databases of the present disclosure can be stored locally, such on the computer or hand held device, or remotely, such as on a file server or main frame computer. It is also an aspect of this disclosure that a fee for access to the database can be charged.

As noted above, nearly all of the clinical applications of D-w MRI employ relative changes of the initial slope of the b-space decay (lima M, and Le Bihan D, Radiology (2016) 278:13-32; Glasser M F, et al., Nat. Neurosci. (2016) 19: 1175-1187; Hamstra D A, et al., Proc. Nat. Acad. Sci. (2005) 102:16759-16764; Le Bihan D, et al., Proc. Nat. Acad. Sci. (2006) 103:8263-8268). Thus the results presented herein demonstrate that many, if not all, of these changes reflect the metabolically active nature of water transport in biological tissue. Water is not simply passively "diffusing" through tissue. Thus the approach disclosed herein can be comprehensively thought of as activity MRI (aMRI).

There is another very important implication of these results. The in vivo mapping of the $k_{io}$ parameter is a new form of metabolic imaging. However, tissues are metabolically inhomogeneous (Springer C S, et al., NMR Biomed. (2014) 27:760-773, Rooney W D, et al., NMR Biomed. (2015) 28:607-623; Li X, et al., J. Magn. Reson. (2016) 269:104-112). The other, elegant metabolic imaging modalities extant (nuclear medicine and MR spectroscopic imaging) lack the spatial resolution required to detect much of the inhomogeneity (Springer C S, et al., NMR Biomed. (2014) 27:760-773; Rooney W D, et al., NMR Biomed. (2015) 28:607-623). But, their derivation from the $^1H_2O$ MR signal allows $k_{io}$ maps to have quite high spatial resolution; generally 1 (mm)$^3$ (=1 μL) voxels or better (Springer C S, et al., NMR Biomed. (2014) 27:760-773; Rooney W D, et al., NMR Biomed. (2015) 28:607-623; Li X et al., J. Magn. Reson. (2016) 269:104-112). Thus, this is new, high-resolution metabolic imaging. Furthermore, the discovery of active trans-membrane water cycling (Zhang Y, et al., Biophys. J. (2011) 101:2833-2842), and its use to not only measure $k_{io}$ in vivo but also map its values, require the injection of exogenous, paramagnetic Gd(III) chelate or Fe(III) contrast agents (Springer C S, et al., NMR Biomed. (2014) 27:760-773; Rooney W D, et al., NMR Biomed. (2015) 28:607-623; Li X, et al., J. Magn. Reson. (2016) 269:104-112; Tudorica A et al., Transl. Onc. (2015) 9:8-17; Ackerman, J J H, NMR Biomed. (2016) 29:4-5). Though these are extremely common in clinical MRI—their administration is minimally invasive, there is increasing concern over unwanted side effects (Kanal E and Tweedle M F, Radiology (2015) 275:630-634). Thus, the aMRI approach introduced here also represents non-invasive, high-resolution metabolic imaging.

EXAMPLES

Example 1

Translocation of Water Molecules in Tissue

Synopsis

Numerical simulations of water molecule translocation are presented. The molecules execute random walks in a 3D ensemble of digital cells with density and size pertinent for biological tissue. The mean net displacements reflect "hindered" or "restricted" translocations for both extra- and intracellular water, characterized by an infinite number of exponentials [or Gaussian functions]. The hindrance is very sensitive to the cell membrane permeability, in the range for tissue—and controlled by active cell metabolism.

Introduction

One of biological tissue's essences is its microscopic compartmentalization: primarily between intra- and extracellular space. Evolution has produced cell membranes relatively impermeable to water and most solute molecules. It has been long recognized that membrane permeability to many solutes is under active metabolic control. In contrast, it has been generally assumed that water molecules cross cell membranes via passive mechanisms. It has been recently recognized, however, that membrane water permeability too is dominated, and thus controlled, by an active metabolic mechanism. The equilibrium cellular water efflux rate constant, $k_{io}$, a measure of the cell membrane water permeability coefficient (PW), is proportional to the cell membrane $Na^+,K_+$-ATPase (NKA) activity, one of biology's most crucial enzymes.

Recent numerical computer simulations of random water molecule displacements in tissue, including provision for $k_{io}$, proved remarkable in describing the absolute transverse $^1H_2O$ relaxation in blood without any adjustable parameters. Here, such simulations are employed for the general case of water translocation in tissue.

Methods

Monte Carlo simulations were run on a hexagonal close-packed ensemble of spheres (radius R=15 μm, intracellular volume fraction, $(v_i)$=0.74). This model is diagrammed in FIG. 1. That cell membranes present hindrance to displacement is evident from rejected crossings in both intra- and extracellular spaces. Simulations were carried out for a 3D ensemble of 10,648 cells. The water diffusion coefficient (D') was set to 1.5 μm$^2$/ms (half the 37° C. pure water value (Ackerman, J J H, Neil J J, NMR Biomed (2010) 23:725-733)). Step duration $(t_s)$ was set to 1 μs, determining the walk root-mean-square straight line segment length $(<l_s>^{rms}=(6D't_s)^{1/2})$ to be 95 nm. The purpose for D' is to define $<l_s>^{rms}$; it has no other physical meaning. The digital permeability was adjusted to provide an average intracellular lifetime $(\tau_i)$, with $k_{io}=1/\tau_i$. Control of $k_{io}$, and $v_i$, is the unique aspect of these simulations. The value of $P_W$ is calculated as $((t_p)D'/<l_s>_{rms})$ or $(2Rk_{io}/6)$; where $t_p$ is the fraction of membrane encounters having a permeation.

Results

Figure 2:
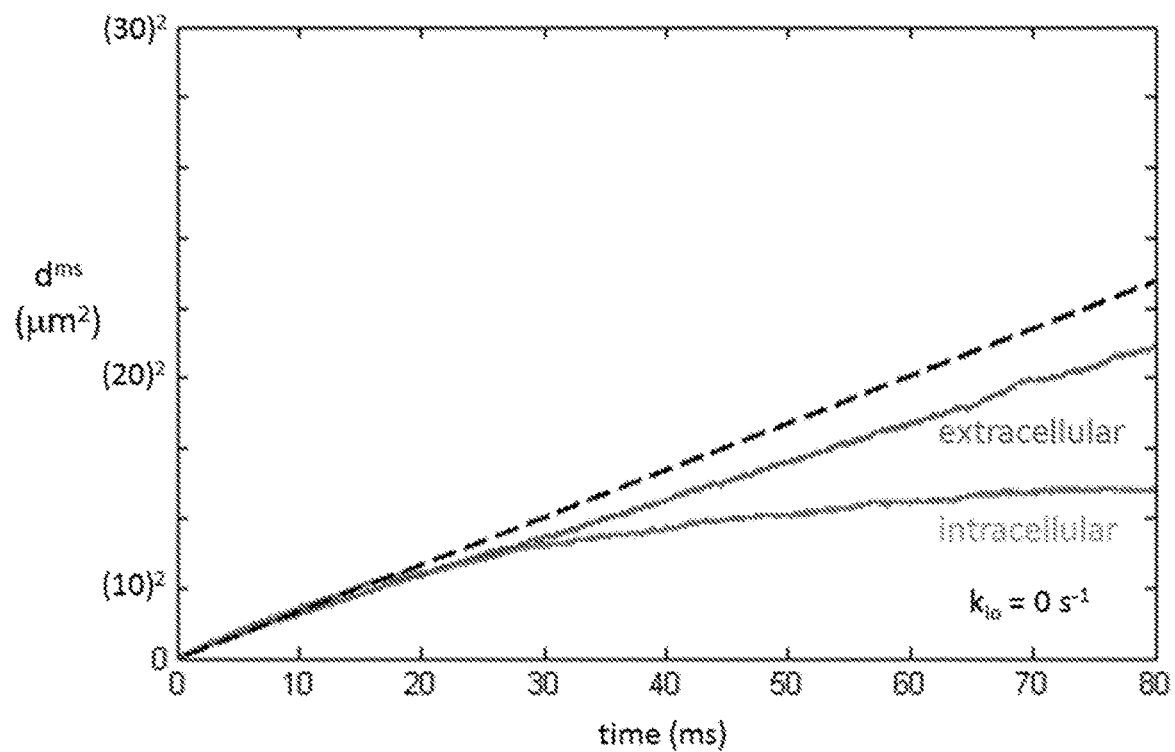
FIG. 2 shows the mean squared displacements, $d^{ms}$ ($\equiv <d^2>$), (note the square-scaled ordinate) as functions of walk duration for water molecules in an ensemble of impermeable cells (intracellular water volume fraction ($v_i$)=0.74 and Radius (R)=15 μm). The curves for extra- and intracellular molecules are labelled. 800 walks were averaged for each plot.

The mean squared displacement ($d^{ms} \equiv <d^2>$) is plotted in FIG. 2 for extra- and intracellular water molecules ($v_i$=0.74 and R=15 μm) when no cell permeation was allowed ($k_{io}$=0 s$^{-1}$). For translocation in homogeneous 3D space, the Einstein equation is: $d^{ms}$=6Dt; where D is the diffusion coefficient and t is the diffusion time (duration). In such a case, the plot of $d^{ms}$ vs. t is a straight line with slope 6D. Neither the extra- nor intracellular FIG. 2 traces are linear. An asymptotic straight dashed line in FIG. 2 makes the extracellular plot nonlinearity evident.

Average squared displacements were calculated for water molecule random walks through the cell ensemble ($v_i$=0.74 and R=15 µm) with varying membrane permeabilities. Results spanning the known range of tissue $k_{io}$ values are plotted in FIG. 3 The $k_{io}$=0 s$^{-1}$ is equivalent to the volume-weighted average (for this macromolecule-free model): $d^{ms}$= $(1-v_i)d_o^{ms}+v_id_i^{ms}$; where $d_o$ and $d_i$ are the extra- and intracellular water molecule $d^{ms}$ values, respectively (FIG. 2). To-date, the extra- and intracellular $^1H_2O$ signals can be reliably discriminated only with sufficiently concentrated extracellular paramagnetic solute.

Discussion

Figure 3:
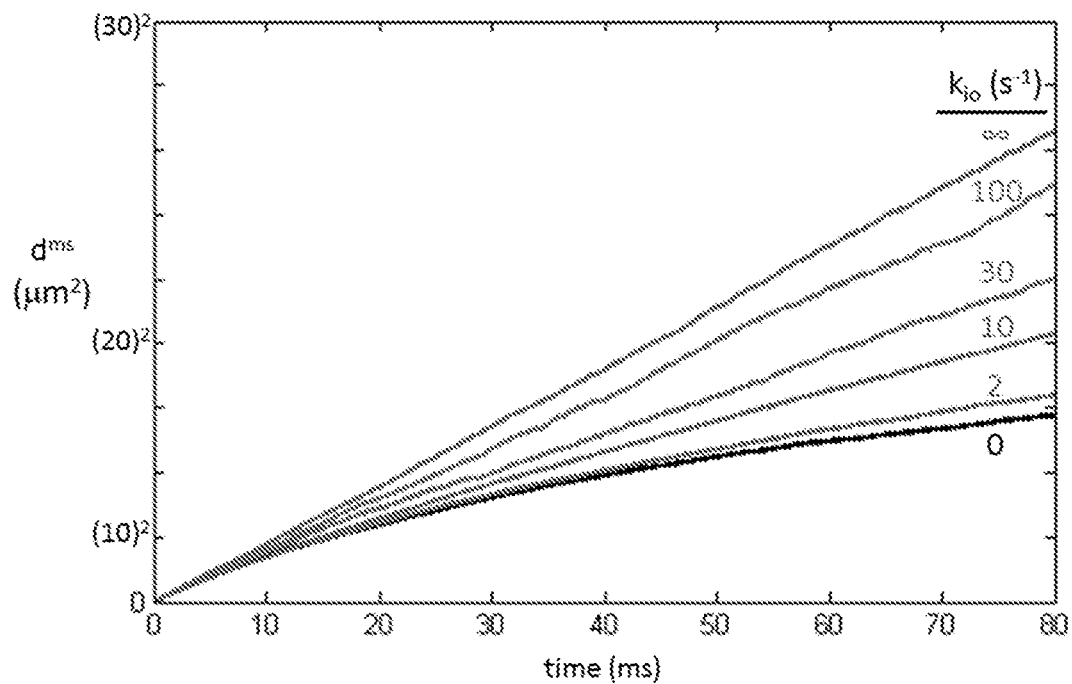
FIG. 3 shows the mean square displacements, $d^{ms}$ ($\equiv <d^2>$), (note the square-scaled ordinate) as a function of walk duration for water molecules in a cell ensemble ($v_i$=0.74 and R=15 μm) with varying cell membrane water permeabilities: $k_{io}$=0, 2, 10, 30, and 100 s$^{-1}$, and $k_{io}$=∞. The parameter $k_{io}$ is the unidirectional rate constant for equilibrium cellular water efflux. It is proportional to the water permeability coefficient, $P_W$. Each curve results from the averaging of at least 1000 random walks.

Only the $k_{io}$=∞ plot in FIG. 3 is linear. This is the case for "free" diffusion: slope 6D'. All the others are curved, as are the FIG. 2 plots. Such curvature is the signature of "hindered" or "restricted" diffusion (multiple Gaussian processes). A straight $d^{ms}$ vs. t plot is indicative of the single exponential nature of the Einstein equation. A continuously curved plot reflects an infinite number of exponentials; there are an infinite number of D values as the instantaneous tangent continually decreases. This is not a bi-exponential curve though it has often been incorrectly fitted with an empirical bi-exponential function. A corollary is that the diffusion coefficient, D, is defined only for "free" diffusion (slope/6).

These results indicate D is not defined for water translocation in tissue—either intra- or extracellular. This has important implications, as much of the D-weighted MRI literature has been concerned with differences of D values for intra- and extracellular water molecules. This new insight into the membrane permeability dependence of tissue water displacement provides a basis for novel methods for detecting cell metabolic activity.

Example 2

Molecular Description of Diffusion-Weighted Tissue Water Signals

Synopsis

Monte Carlo simulations of water molecule random walks in an ensemble of close-packed cells (of the density and size pertinent for tissue) were used to investigate determinants of the decay of the diffusion-weighted $^1H_2O$ signal in b-space. The decay is characterized by an infinite number of exponentials; it is not bi-exponential. It was found that the decay strongly depends on $k_{io}$, the equilibrium cellular water efflux rate constant—a measure of cell membrane water permeability and Na$^+$,K$^+$-ATPase activity. The latter is a vital enzyme flux in biology.

Introduction

Diffusion-weighted (D-w) tissue $^1H_2O$ signals underlie important clinical MRI applications. However, there is concern over unsatisfactory biophysical/molecular explanations for the signal's fundamental nature. Numerical computer simulations of random tissue water displacements provide a remarkably accurate description of blood $^1H_2O$ transverse relaxation with no adjustable parameters. These include $k_{io}$, the rate constant for equilibrium cellular water efflux, measuring the cell membrane water permeability coefficient, $P_W$. $k_{io}$ is proportional to cell membrane Na$^+$,K$^+$-ATPase (NKA) activity, one of biology's most vital fluxes. Here, such simulations are employed to elaborate D-w tissue $^1H_2O$ signals.

Methods 80 ms water random walks in 10,648 hexagonal close-packed spherical (15 µm radius, R) cell ensemble experienced an intracellular volume fraction ($v_i$)=0.74. The 1 µs step duration ($t_s$) determines the walk root-mean-square segment length ($<I_s>^{rms}$=(6D'$t_s$)$^{1/2}$) as 95 nm when D'=1.5 µm$^2$/ms. The only purpose for this diffusion coefficient (D') is to define $<I_s>^{rms}$; it has no physical meaning. The simulated permeability was adjusted to different values: $P_W$ is ((tp)D'/$<I_s>^{rms}$); where $t_p$ is the fraction of membrane encounters having a permeation, and $k_{io}$=6P$_W$/(2R). A diffusion-encoding spin-echo pulse sequence was simulated; with two pulsed magnetic field gradients (duration δ=20 ms, leading edges separated by Δ=50 ms). This encodes positional information in the $^1H_2O$ spin precessional phase. For b values from 0-10 ms/µm$^2$, the gradient strength, G, was calculated using b≡(γGδ)$^2$t$_D$; where γ is the $^1$H magnetogyric ratio, and $t_D$≡(Δ-(δ/3)).

Results

FIG. 4 shows the log D-w H$_2$O signal b-dependence for four $k_{io}$ values. The $k_{io}$=∞ plot is linear, as expected for "free" diffusion. For infinite and zero $k_{io}$, the plots curve upward. Also plotted are experimental data from human cortical gray matter (GM). The cerebral $k_{io}$ is 1.81 s$^{-1}$ (44 µL ROI in anesthetized rat brain—mostly GM-like), and $v_i$=0.81. The agreement between the $k_{io}$=2 s$^{-1}$ decay (FIG. 4) and independent GM data (solid points) is remarkable, since no formal "fitting" was employed. The residuals' systematic nature (negative for b<2, positive for b>2) suggests the data could be better fitted by relatively small adjustments of $v_i$ and/or R. For example, changing $v_i$ from 0.74 to the known 0.81 might suffice. This would require deforming the cells into a non-spherical shape and running simulations again. For example, the digital cells could be deformed into "spherical cuboids," a shape that is intermediate between spherical (for which $v_i$=0.74) and cubic (for which $v_i$=1.0).

Figure 6:
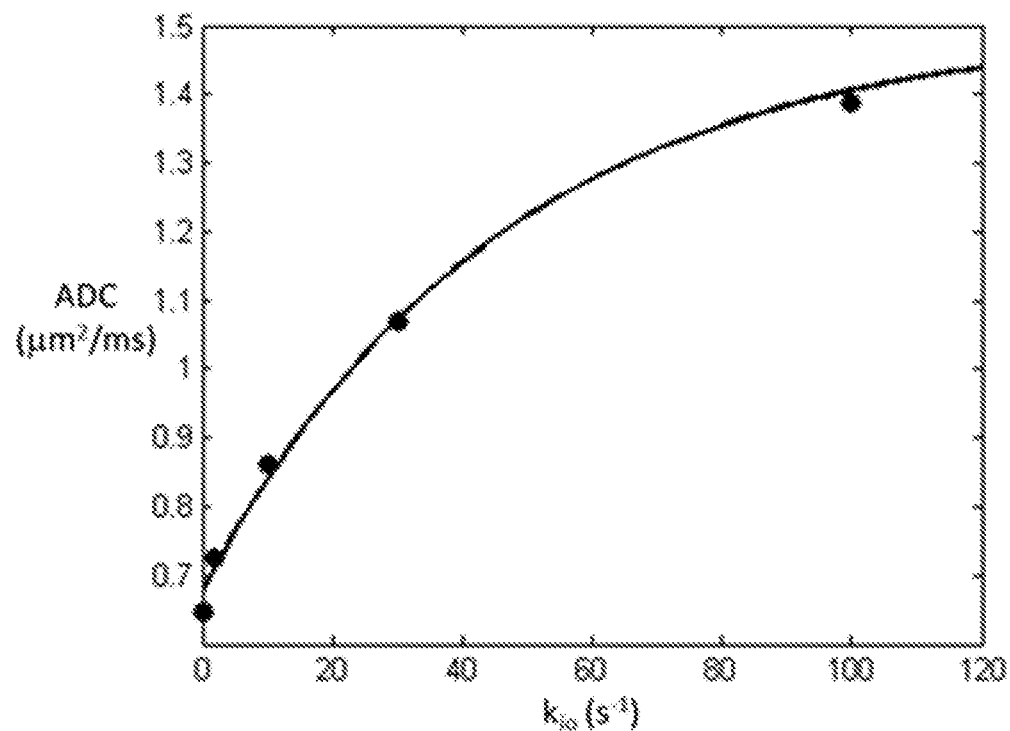
FIG. 6 shows a plot of simulated ADC vs. $k_{io}$. The sensitivity of ADC to $k_{io}$ is quite evident, particularly for low $k_{io}$ values observed in tissue. The solid curve is meant only to guide the eye.

The initial b-space decay is remarkably $k_{io}$-sensitive (FIG. 5). The negative asymptotic slope is often termed the Apparent Diffusion Coefficient (ADC), and—though difficult to accurately measure—is often used clinically. ADC values determined from FIG. 5 are shown in FIG. 6. It is noteworthy that the $k_{io}$ range known for tissue, 1-20 s$^{-1}$ exhibits the greatest sensitivity in these simulations. Testing of the $v_i$ and R sensitivities can also be readily performed.

Discussion

Only the $k_{io}$=plot (FIGS. 4 and 5) is straight, representing "free" diffusion with slope –D'. The other plots' curvature is the signature for "hindered" or "restricted" diffusion. A linear semilog (S/S$_0$) vs. b plot indicates a single decay exponential. A continuously curved plot reflects an infinite number of exponentials [Gaussians]; the instantaneous tangents become continuously less negative with increasing b. This corresponds to an infinite number of "D" values. The diffusion coefficient, D, is defined for only "free" diffusion: i.e. the –slope. These results suggest that $k_{io}$, $v_i$, and R are major intrinsic determinants of D-w tissue $^1H_2O$ signals. These are important biomarkers. $k_{io}$ is proportional to the cellular metabolic NKA rate (cMR$_{NKA}$). The $v_i$ quantity is equal to the product of the cell number density (ρ) and average cell volume <V>, i.e. ρ<V>; ρ is a quantitative "cellularit" measure, R is proportional to V$^{1/3}$, and V reports edema. Since even the highest resolution $^1H_2O$ MRI voxel contains 10$^5$-10$^6$ cells it is understood that voxel averages, <$k_{io}$>, <$v_i$>, and <R> will result when simulated b-space decays are fitted to data voxel-by-voxel. These results indicate D cannot be defined for water translocation in tissue— either intra- or extracellular. This has important implications. Much of the D-weighted MRI literature has been concerned with differences of D values for intra- and extracellular water.

Example 3

Non-Invasive Determination of Sodium Pump Activity In Vivo with D-w MRI

Synopsis

Using a simple model, Monte Carlo random walk simulated D-w MRI b-space decays exhibit sensitivity to parameters measuring membrane Na,K-ATPase activity, cell density, and voxel average cell volume. Furthermore, the simulation matching the literature experimental in vivo human cerebral cortex b-space decay has model parameters in near absolute agreement with the most pertinent literature values. The model parameters are: $k_{io}$=2 s$^{-1}$, $\rho$=80,400 cells/µL, and V=9.2 pL. In addition, the ADC of this simulation agrees with published results.

Introduction

Perhaps biology's most vital enzyme is the cell membrane Na$^+$,K$^+$-ATPase [NKA], which maintains the ion gradients and membrane potential. Yet, it has never been possible to measure the cellular metabolic NKA rate, $^cMR_{NKA}$, in vivo. Recent results (for example, Springer, et al, *NMR Biomed* 27: 760-773 (2014); incorporated by reference herein) suggest the steady-state cellular water efflux rate constant, $k_{io}$, has a $^cMR_{NKA}$ contribution. If $k_{io}$ is expressed as having both an active and passive component in the form $k_{io}=k_{io}(a)+k_{io}(p)$, where $k_{io}(a)$ and $k_{io}(p)$ are the energetically active and passive components, respectively, then $k_{io}$ may be further cast as follows:

$$k_{io} = \left\{\frac{x}{[H_2O_i]\cdot V}\right\}^c MR_{NKA} + \left(\frac{A}{V}\right)P_W(p)$$

here x is the stoichiometric mole ratio H$_2$O(cycled)/ATP (consumed), [H$_2$O$_i$] is the intracellular water concentration (~30 M, ~30 fmol (H$_2$O)/fL (cell)), A and V are the voxel average cell surface area and volume, respectively, $^cMR_{NKA}$ is the cellular NKA metabolic rate (e.g., fmol(ATP)/s/cell), and P$_W$(p) the passive cell membrane water permeability coefficient. The fundamental tissue properties for mean cell volume, V, and cell density, $\rho$ [cells/µL], have also not been measurable in vivo.

Methods

A straightforward Monte Carlo random walk approach can evaluate $k_{io}$, $\rho$, and V (see Wilson, et al, *MRM* 77: 2015-2027 (2017) and Wilson, et al, *Proc. ISMRM* 25: 1738 (2017); both incorporated by reference herein). Accordingly, a simulation of water molecule displacements was conducted within a 3D ensemble of 10,648 identical spheres having hexagonal close-packed symmetry (see Clark and Le Bihan, *MRM* 44: 852-859 (2000); incorporated by reference herein); a primitively simple, parsimonious approach with no vasculature or intrinsic anisotropy. The 37° C. pure water diffusion coefficient, D$_0$=3.0 µm$^2$/ms, was used for all particles, whether inside or outside cells.

Results

FIGS. 7A, 7B, and 7C present simulation families varying, in turn, $k_{io}$, $\rho$, and V. The ordinates measure log[S/S$_0$], where S and S$_0$ are the D-w and total transverse signal intensities: the abscissae report normalized coherence decay, b [$\equiv(\gamma G\delta)^2 t_D$: $\gamma$ is the $^1$H magnetogyric ratio, G and $\delta$ the PFG strength and duration, and the diffusion time $t_D\equiv$ [$\Delta-(\delta/3)$], $\Delta$ is the interval between the PFG pair leading edges]. In FIG. 7A, decays for five $k_{io}$ values are shown with V fixed at 9.2 pL [cell radius, R=13 µm] and $\rho$ at 80,400 cells/µL [$\rho$=v$_i$/V: the intracellular volume fraction, v$_i$=0.74; the cells touched]. Non-linear, non-Gaussian decays in these semi-log plots are $k_{io}$-sensitive. The ADC (apparent diffusion coefficient; the negative of the asymptotic {ln(S/S$_o$)/b} slope) increases with $k_{io}$ for constant $\rho$ and V (FIG. 8A). This is sensible: on the average, water molecules can move further, and de-phase more, the more permeable the cell membranes. In FIG. 7B, decays for five $\rho$ values are shown with V fixed at 9.2 pL and $k_{io}$ at 2.0 s$^{-1}$. [For $\rho$=97,800 cells/µL, the spheres were slightly deformed toward cubes (dashed curve): v of 0.90 [(97.8×10$^3$ cells/µL (tissue)) (9.2× 10$^{-6}$ µL/cell)] is not achievable with close-packed spheres.] The decay for $\rho$=0 (i.e., pure water) is linear; a Gaussian diffusion process with ADC=D$_0$. For fixed $k_{io}$ and V, ADC decreases with increasing $\rho$ (FIG. 8B). This is also sensible: water molecules cannot translate as well with greater cellularity. But, the FIG. 8B span is 45,400 cells/µL, a very large $\rho$ increase (a typical human $^1$H$_2$O MR voxel is 1 µL). In FIG. 7C, decays for four V values are shown, with $\rho$ fixed at 80,400 cells/µL and $k_{io}$ at 2.0 s$^{-1}$. At small b, cell swelling decreases ADC (in accordance with conventional wisdom; FIG. 8C) but increases it at larger b values. The range from 4.2 to 9.2 pL is a more than V doubling; a large increase.

Discussion

FIGS. 7A, 7B, and 7C also show well-validated data from a 3.3 mL human cerebral cortex ROI in vivo (denoted as diamonds on the plots). The agreement of one of the simulation curves in each panel (i.e., the curves for $k_{io}$=2.0 s$^{-1}$, $\rho$=80,400 cells/µL, and V=9.2 pL of FIGS. &A, 7B, and 7C, respectively) with experimental data, especially at clinical b (below ~2.5 ms/(µm)$^2$=2500 s/(mm)$^2$), is apparent. Besides matching the data, the parameters for these simulations ($k_{io}$=2.0 s$^{-1}$, $\rho$=80,400 cells/µL, V=9.2 pL) are in near absolute agreement with the most pertinent literature, as presented in Table 1. This includes the corresponding ADC value, which is 0.74 (µm)$^2$/ms. This agreement with the data was achieved without executing a formal fitting.

TABLE 1

| | | Fundamental Tissue Cellular Properties Fundamental Tissue Cellular Properties | |
|---|---|---|---|
| $k_{io}$ | 1.81 s$^{-1}$ | ventricular CA-injected, anesthetized rat brain | Quirk, et al, MRM 50: 493-499(2003) |
| | 2.02 s$^{-1}$ | CA-perfused, functioning rat brain slices | Bai, et al, PISMRM 25: 203(2017) |
| $\rho$ | 88,000 cells/µL | isotropic fractionator histology, primate premotor cortex | Collins, et al, PNAS 113: 740-745 (2016) |
| V | 1-15 pL | cell volume distribution medians, optical microscopy of cell cultures | Milo, et al, Cell Biology by the Numbers, pp. 15, 16 (2016) |
| ADC | 0.83 (µm)$^2$/ms | 1/3 Trace of D tensor, awake human cortex | Pierpaoli, et al, Radiology 201: 637-648 (1996) |

An overall picture from FIGS. 7A, 7B, and 7C is the major determinants of tissue ADC are the "concentration" of membranes [inversely], and their permeability [directly], with interesting implications for a number of D-w MRI applications. One can distinguish acute and chronic ADC changes, as compiled in Table 2.

TABLE 2

Acute and Chronic ADC Changes
ADC Changes acute

| | | | |
|---|---|---|---|
| stroke | −30% [< 2 hrs] | human | Ackerman, Neil, NMRB 23: 725-733 (2010) |
| direct brain ouabain injection | −39% [< 15 min] | rat | Veldhuis, et al, JCBFM 23: 62-74 (2003) |
| sudden death | −42% | rat | Meier, et al, MRM 50: 500-509 (2003) |
| | −44% | rat | Pfeuffer, et al, MAGMA 8: 98-108 (1999) |
| DFMRI | anesthesia, sedation | rat | Abe, et al, PLOSBiol 15: e2001494 (2017) |
| | stimulus response | human | Le Bihan, et al, PNAS 103: 8263-8268 (2006) |
| | genetically engineered, change | mouse | Schilling, et al, Nature Biotech 35: 75-80 (2017) |
| | triggered specific $k_{io}(p)$ | mouse | Mukherjee, et al, Nature Comm 7: 13891 (2016) | chronic

| | | | |
|---|---|---|---|
| cancer | decreases with progression | human | lima, Le Bihan, Radiology 278: 13-32 (2016) |
| | increases with Tx | human | Moffat, et al, PNAS 102: 5524-5599 (2005) |

Since $^cMR_{NKA}$ controls major osmolyte fluxes (e.g., 25 billion Na$^+$ and K$^+$ ions (cycled)/s/cell), $k_{io}(a)$ could change very quickly. Fast V changes are often invoked, and this is possible. However, note that these would have to be rather large, and averaged over 104 to 10$^5$ cells/voxel. For example, it is interesting that the ADC decrease caused by direct injection of the specific NKA inhibitor ouabain is similar to that for stroke, and for sudden death (Table 2.). V changes occur, but are likely not causative for ADC changes (see Ackerman and Neil, *NMR Biomed* 23: 725-733 (2010); incorporated by reference herein). In no case has a $k_{io}$ change been found due solely to the V change. At the other extreme, the large ρ changes required [>10$^3$ cells/voxel] must certainly be chronic. The prime example is in oncology, also shown in Table 2. Pure cancer loci can exceed 10$^6$ (small)cells/μL. However, $k_{io}$ should be much more quickly responsive to therapy (see Tudorica, et al, *Trans Oncol* 9: 8-17 (2015); incorporated by reference herein).

Example 4

Exemplary Computing System

In some embodiments, the above described methods and processes may be tied to a computing system, including one or more computers. In particular, the methods and processes described herein, e.g., methods described herein, may be implemented as a computer application, computer service, computer API, computer library, and/or other computer program product.

Figure 9:
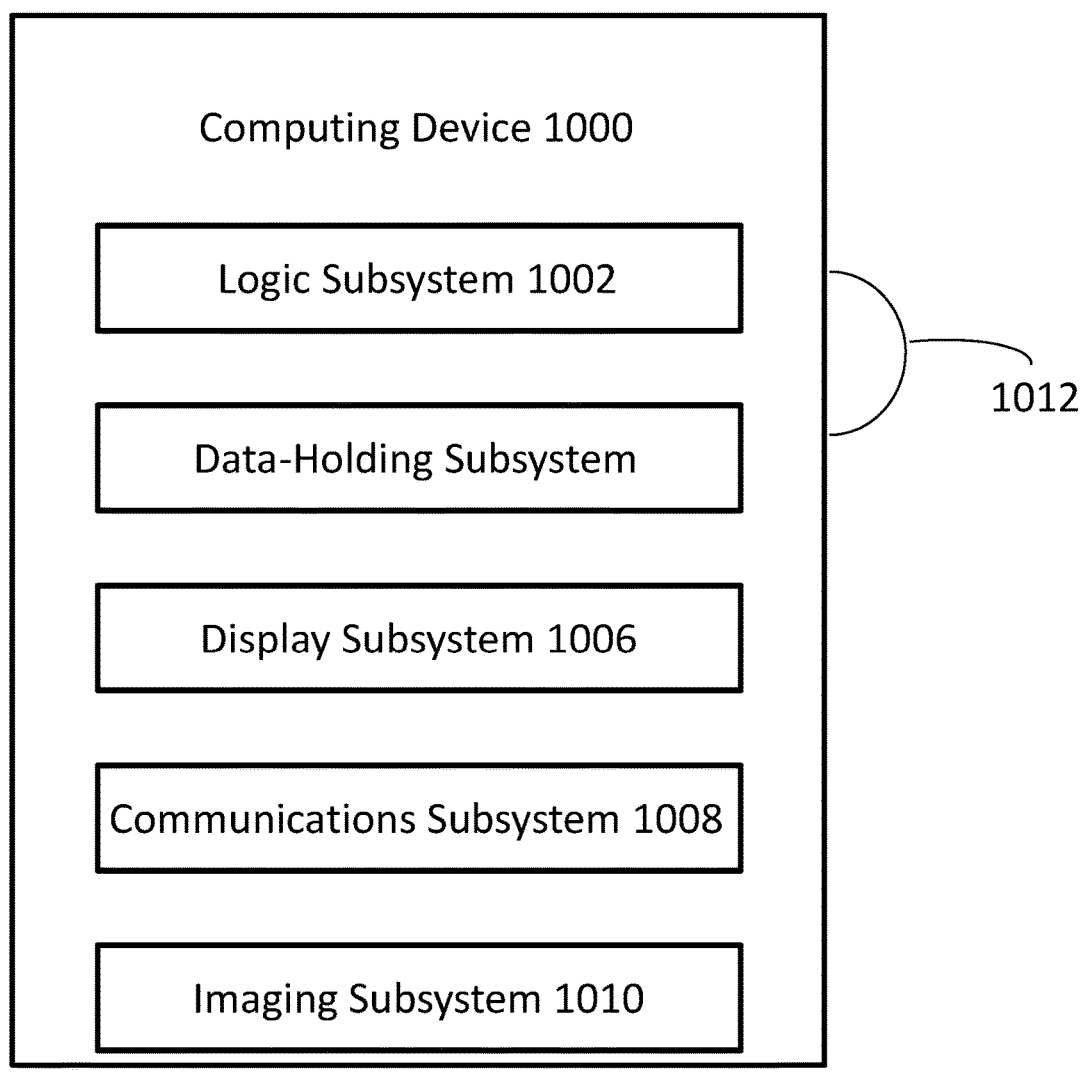
FIG. 9 schematically shows an example of a computing system, in accordance with the disclosure.

FIG. 9 schematically shows a non-limiting computing device 1000 that may perform one or more of the above described methods and processes 1000. For example, computing device 1000 may represent a processor, and may be operatively coupled to, in communication with, or included in an MRI system. Computing device 1000 is shown in simplified form. It is to be understood that virtually any computer architecture may be used without departing from the scope of this disclosure. In different embodiments, computing device 1000 may take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1000 includes a logic subsystem 1002 and a data-holding subsystem 1004. Computing device 1000 may optionally include a display subsystem 1006, a communication subsystem 1008, an imaging subsystem 1010, and/or other components not shown in FIG. 9. Computing device 1000 may also optionally include user input devices such as manually actuated buttons, switches, keyboards, mice, game controllers, cameras, microphones, and/or touch screens, for example.

Logic subsystem 1002 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions, for example stored on drives and other associated computer readable media providing nonvolatile storage of data, data structures (databases) libraries, computer executable instructions, etc. For example, the one or more processors may comprise physical circuitry programmed to perform various acts described herein. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 1004 may include one or more physical, non-transitory, devices configured to hold data and/or instructions executable by the logic subsystem to implement the herein described methods and processes. When such methods and processes are implemented, the state of data-holding subsystem 1404 may be transformed (e.g., to hold different data).

Data-holding subsystem 1004 may include removable media and/or built-in devices. Data-holding subsystem 1004 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1004 may include devices with one or more of the following characteristics: volatile, nonvolatile, dynamic, static, read/write, read-only, random access, sequential access, location addressable, file addressable, and content addressable. In some embodiments, logic subsystem 1002 and data-holding subsystem 1004 may be integrated into one or more common devices, such as an application specific integrated circuit or a system on a chip.

FIG. 9 also shows an aspect of the data-holding subsystem in the form of removable computer-readable storage media 1012, which may be used to store and/or transfer data and/or instructions executable to implement the herein described methods and processes. Removable computer-readable storage media 1012 may take the form of CDs, DVDs, HD-DVDs, Blu-Ray Discs, EEPROMs, flash memory cards, USB storage devices, and/or floppy disks, among others.

When included, display subsystem 1006 may be used to present a visual representation of data held by data-holding subsystem 1004. As the herein described methods and processes change the data held by the data-holding subsystem, and thus transform the state of the data-holding subsystem, the state of display subsystem 1006 may likewise be transformed to visually represent changes in the underlying data. Display subsystem 1006 may include one or more display devices utilizing virtually any type of technology. Such display devices may be combined with logic subsystem 1002 and/or data-holding subsystem 1004 in a shared enclosure, or such display devices may be peripheral display devices.

When included, communication subsystem 1008 may be configured to communicatively couple computing device 1000 with one or more other computing devices. Communication subsystem 1008 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing device 1000 to send and/or receive messages to and/or from other devices via a network such as the Internet.

Portions of the software for constructing a three-dimensional electronic library of simulated decays of the diffusion-weighted $^1H_2O$ signal in b-space as well as databases, and/or libraries storing the simulation, as well as software for querying such libraries or databases can be-implemented in a single computer system or a distributed to other computer system.

When included, imaging subsystem 1010 may be used acquire and/or process any suitable image data from various sensors or imaging devices in communication with computing device 1000. For example, imaging subsystem 1010 may be configured to acquire MRI image data, as part of an MRI system. Imaging subsystem 1010 may be combined with logic subsystem 1002 and/or data-holding subsystem 1004 in a shared enclosure, or such imaging subsystems may comprise periphery imaging devices. Data received from the imaging subsystem may be held by data-holding subsystem 1004 and/or removable computer-readable storage media 1012, for example.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method of preparing a parametric tissue map for tissue in a subject, comprising:
   receiving, with one or more computing devices, Diffusion-weighted Magnetic Resonance Imaging (D-w MRI) acquisition data comprising a diffusion-weighted $^1H_2O$ signal;
   determining, with one or more computing devices, a b-space decay of one or more voxels in the D-w MRI acquisition data, wherein the b-space decay is a decay of log(S/S0) relative to b, S is the diffusion-weighted $^1H_2O$ signal, S0 is a maximum value of the diffusion-weighted $^1H_2O$ signal, and b is a product of a diffusion time and a square of a gradient effectiveness; and
   selecting, with one or more computing devices, a simulated decay of the diffusion-weighted $^1H_2O$ signal in b-space from an electronic library of simulated decays of the diffusion-weighted $^1H_2O$ signal in b-space that matches the b-space decay of the one or more voxels in the D-w MRI acquisition data, thereby preparing one or more parametric tissue maps of the D-w MRI acquisition data.

2. The method of claim 1, wherein the electronic library is generated from a model of water molecules in an ensemble of close-packed cells within a magnetic field, the cells modeled with a mean radius (R) and a rate constant for equilibrium cellular water efflux ($k_{io}$), and an intracellular volume fraction ($v_i$).

3. The method of claim 2, wherein the close packed cells are spherical cells.

4. The method of claim 2, wherein the mean radius (R) is about 15 μm.

5. The method of claim 2, wherein the mean radius (R) is in a range 3 μm to 20 μm.

6. The method of claim 2, wherein the cells are polygonal.

7. The method of claim 2, wherein the cells are non-uniform in size and non-periodically spaced.

8. The method of claim 2, wherein the intracellular volume fraction ($v_i$) is about 0.74.

9. The method of claim 2, wherein the rate constant for equilibrium cellular water efflux, $k_{io}$, is in a range 0.0 to 100 sec$^{-1}$.

10. The method of claim 1, wherein the electronic library of simulated decays of the diffusion-weighted $^1H_2O$ signal in b-space are parameterized according to:
    a rate constant for equilibrium cellular water efflux ($k_{io}$) with V and ρ fixed, wherein V is a mean cell volume and ρ is a cell number density,
    the cell number density (ρ) with V and $k_{io}$ fixed, and
    the mean cell volume (V) with ρ and $k_{io}$ fixed.

11. The method of claim 1, wherein the one or more parametric tissue maps show a rate constant for equilibrium cellular water efflux ($k_{io}$) as a function of position when overlayed on an MRI image.

12. The method of claim 1, wherein the electronic library of simulated decays of the diffusion-weighted $^1H_2O$ signal in b-space are parameterized according to a rate constant for equilibrium cellular water efflux ($k_{io}$), an intracellular volume fraction ($v_i$), and a mean cell volume (V).

13. The method of claim 1, wherein the one or more parametric tissue maps comprise a parametric mapping of $k_{io}$, a rate constant for equilibrium cellular water efflux, to provide a contrast agent-free method of in vivo metabolic imaging.

14. The method of claim 1, wherein the simulated decays describe an absolute transverse $^1H_2O$ relaxation in blood without any adjustable parameters.

15. The method of claim 1, wherein the library of simulated decays of the diffusion-weighted $^1H_2O$ signal in b-space comprises:
- simulated decays of log(S/S0) relative to b for different values of $k_{io}$ with V and ρ fixed, wherein $k_{io}$ is a rate constant for equilibrium cellular water efflux, V is a mean cell volume, and ρ is a cell number density;
- simulated decays of log(S/S0) relative to b for different values of ρ with V and $k_{io}$ fixed; and
- simulated decays of log(S/S0) relative to b for different values of V with ρ and $k_{io}$ fixed.

16. The method of claim 15, wherein the selecting comprises identifying:
- one of the simulated decays of log(S/S0) relative to b for the different values of $k_{io}$ with V and ρ fixed;
- one of the simulated decays of log(S/S0) relative to b for the different values of ρ with V and $k_{io}$ fixed; and
- one of the simulated decays of log(S/S0) relative to b for the different values of V with ρ and $k_{io}$ fixed.

17. The method of claim 1, wherein the one or more parametric tissue maps comprise voxel-averaged values of a rate constant for equilibrium cellular water efflux $k_{io}$, a mean cell volume V, and a cell number density ρ.

18. A computer readable media, comprising a non-transitory, computer-readable storage medium having computer-executable program instructions embodied therein for a method of preparing a parametric tissue map for tissue in a subject, comprising instructions for:
- receiving Diffusion-weighted Magnetic Resonance Imaging (D-w MRI) acquisition data comprising a diffusion-weighted $^1H_2O$ signal;
- determining a b-space decay of one or more voxels in the D-w MRI acquisition data, wherein the b-space decay is a decay of log(S/S0) relative to b, S is a signal intensity of the diffusion-weighted $^1H_2O$ signal, S0 is a signal intensity of the diffusion-weighted $^1H_2O$ signal immediately after coherence creation, and b is a normalized coherence decay measure; and
- selecting a simulated decay of the diffusion-weighted $^1H_2O$ signal in b-space from an electronic library of simulated decays of the diffusion-weighted $^1H_2O$ signal in b-space that matches the b-space decay of the one or more voxels in the D-w MRI acquisition data, thereby preparing one or more parametric tissue maps of the D-w MRI acquisition data.

19. The computer readable media of claim 18, wherein the electronic library is generated from a model of water molecules in an ensemble of close-packed cells within a magnetic field, the cells modeled with a mean radius (R) and a rate constant for equilibrium cellular water efflux ($k_{io}$), and an intracellular volume fraction ($v_i$).

20. The computer readable media of claim 19, wherein the mean radius is about 15 μm and the intracellular volume fraction ($v_i$) is about 0.74.

21. The computer readable media of claim 18, wherein the electronic library of simulated decays of the diffusion-weighted $^1H_2O$ signal in b-space are parameterized according to a rate constant for equilibrium cellular water efflux ($k_{io}$), a cell number density (ρ), and a mean cell volume (V).

22. The computer readable media of claim 18, wherein the one or more parametric tissue maps show rate constant for equilibrium cellular water efflux ($k_{io}$) as a function of position when overlayed on an MRI image.

23. The computer readable media of claim 18, wherein the electronic library of simulated decays of the diffusion-weighted $^1H_2O$ signal in b-space are parameterized according to a rate constant for equilibrium cellular water efflux ($k_{io}$), an intracellular volume fraction ($v_i$), and a mean cell volume (V).

24. The computer readable media of claim 18, wherein parametric mapping of a rate constant for equilibrium cellular water efflux parameter, $k_{io}$, provides a contrast agent-free method of in vivo metabolic imaging.

25. The computer readable media of claim 18, wherein:
- the library of simulated decays of the diffusion-weighted $^1H_2O$ signal in b-space comprises simulated decays of log(S/S0) relative to b for different values of $k_{io}$ with V and ρ fixed, wherein $k_{io}$ is a rate constant for equilibrium cellular water efflux, V is a mean cell volume, and ρ is a cell number density; and
- the selecting comprises identifying one of the simulated decays of log(S/S0) relative to b for the different values of $k_{io}$ with V and ρ fixed.

26. The computer readable media of claim 18, wherein:
- the library of simulated decays of the diffusion-weighted $^1H_2O$ signal in b-space comprises simulated decays of log(S/S0) relative to b for different values of ρ with V and $k_{io}$ fixed, wherein $k_{io}$ is a rate constant for equilibrium cellular water efflux, V is a mean cell volume, and ρ is a cell number density; and
- the selecting comprises identifying one of the simulated decays of log(S/S0) relative to b for the different values of ρ with V and $k_{io}$ fixed.

27. The computer readable media of claim 18, wherein:
- the library of simulated decays of the diffusion-weighted $^1H_2O$ signal in b-space comprises simulated decays of log(S/S0) relative to b for different values of V with ρ and $k_{io}$ fixed, wherein $k_{io}$ is a rate constant for equilibrium cellular water efflux, V is a mean cell volume, and ρ is a cell number density; and
- the selecting comprises identifying one of the simulated decays of log(S/S0) relative to b for the different values of V with ρ and $k_{io}$ fixed.

\* \* \* \* \*